US011395634B2

(12) United States Patent
Mulligan et al.

(10) Patent No.: US 11,395,634 B2
(45) Date of Patent: *Jul. 26, 2022

(54) ESTIMATING PHYSIOLOGICAL STATES BASED ON CHANGES IN CRI

(71) Applicants: Flashback Technologies, Inc., Boulder, CO (US); The Regents of the University of Colorado, a body corporate, Denver, CO (US)

(72) Inventors: Isobel Jane Mulligan, Niwot, CO (US); Gregory Zlatko Grudic, Niwot, CO (US); Steven L. Moulton, Littleton, CO (US)

( * ) Notice: Subject to any disclaimer, the term of this patent is extended or adjusted under 35 U.S.C. 154(b) by 27 days.

This patent is subject to a terminal disclaimer.

(21) Appl. No.: 15/261,661

(22) Filed: Sep. 9, 2016

(65) Prior Publication Data

US 2016/0374625 A1 Dec. 29, 2016

Related U.S. Application Data

(63) Continuation-in-part of application No. 14/885,888, filed on Oct. 16, 2015, and a continuation-in-part of
(Continued)

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *A61B 5/02028* (2013.01);
(Continued)

(58) Field of Classification Search
CPC ............ G06F 19/3437; A61B 5/02028; A61M 5/1723
See application file for complete search history.

(56) References Cited

U.S. PATENT DOCUMENTS 4,930,517 A 6/1990 Cohen et al.
5,074,310 A 12/1991 Mick
(Continued)

FOREIGN PATENT DOCUMENTS

CA 2871608 2/2021
EP 3468457 4/2019
(Continued)

OTHER PUBLICATIONS

International Search Report and Written Opinion prepared by the Korean Intellectual Property Office as International Searching Authority for PCT International Patent Application No. PCT/US2016/051130, dated Dec. 8, 2016, 14 pages.
(Continued)

*Primary Examiner* — Tse W Chen
*Assistant Examiner* — Michael A Catina
(74) *Attorney, Agent, or Firm* — Capitol Patent & Trademark Law Firm, PLLC

(57) ABSTRACT

Novel tools and techniques are provided for assessing, predicting and/or estimating a physiological state of a patient, based on variance of the patient's compensatory reserve index ("CRI") before, during, and/or after a physical perturbation. In some embodiments, the system might receive a first set of physiological data from one or more sensors at a first time relative to a physical perturbation of the patient, and might calculate a first set of CRI values of the patient. The system might receive a second set of physiological data at a second time relative to the physical perturbation, calculate a second set of CRI values, analyze the two sets of CRI values against a pre-existing model, estimate a physiological state (e.g., hydration, etc.) of the patient, and display the estimate on a display device. The system might also control an infusion device to infuse fluids into the patient based on estimated hydration state.

29 Claims, 20 Drawing Sheets

Related U.S. Application Data application No. 14/885,891, filed on Oct. 16, 2015, which is a continuation-in-part of application No. 14/542,426, filed on Nov. 14, 2014, and a continuation-in-part of application No. 14/542,423, filed on Nov. 14, 2014, which is a continuation-in-part of application No. 14/535,171, filed on Nov. 6, 2014, which is a continuation-in-part of application No. 13/554,483, filed on Jul. 20, 2012, now Pat. No. 9,757,041, which is a continuation-in-part of application No. 13/041,006, filed on Mar. 4, 2011, which is a continuation-in-part of application No. 13/028,140, filed on Feb. 15, 2011, now Pat. No. 8,512,260, which is a continuation-in-part of application No. PCT/US2009/062119, filed on Oct. 26, 2009.

(60) Provisional application No. 62/349,516, filed on Jun. 13, 2016, provisional application No. 62/216,187, filed on Sep. 9, 2015, provisional application No. 62/064,809, filed on Oct. 16, 2014, provisional application No. 62/064,816, filed on Oct. 16, 2014, provisional application No. 61/905,727, filed on Nov. 18, 2013, provisional application No. 61/904,436, filed on Nov. 14, 2013, provisional application No. 61/900,980, filed on Nov. 6, 2013, provisional application No. 61/614,426, filed on Mar. 22, 2012, provisional application No. 61/510,792, filed on Jul. 22, 2011, provisional application No. 61/310,583, filed on Mar. 4, 2010, provisional application No. 61/305,110, filed on Feb. 16, 2010, provisional application No. 61/252,978, filed on Oct. 19, 2009, provisional application No. 61/166,499, filed on Apr. 3, 2009, provisional application No. 61/166,472, filed on Apr. 3, 2009, provisional application No. 61/166,486, filed on Apr. 3, 2009, provisional application No. 61/109,490, filed on Oct. 29, 2008.

(51) Int. Cl.

| | | |
|---|---|---|
| *A61B 5/02* | (2006.01) | |
| *G16H 50/20* | (2018.01) | |
| *G16H 50/50* | (2018.01) | |
| *A61B 5/024* | (2006.01) | |
| *A61B 5/022* | (2006.01) | |
| *A61B 7/04* | (2006.01) | |
| *A61B 5/1455* | (2006.01) | |
| *A61M 1/16* | (2006.01) | |
| *A61B 5/029* | (2006.01) | |
| *A61B 5/03* | (2006.01) | |
| *G16H 20/17* | (2018.01) | |
| *G16H 20/30* | (2018.01) | |
| *A61B 5/318* | (2021.01) | |
| *A61B 5/369* | (2021.01) | |
| *A61B 5/398* | (2021.01) | |

(52) U.S. Cl.
CPC ........ *A61B 5/02042* (2013.01); *A61B 5/4848* (2013.01); *A61B 5/4875* (2013.01); *G16H 50/20* (2018.01); *G16H 50/50* (2018.01); *A61B 5/002* (2013.01); *A61B 5/029* (2013.01); *A61B 5/02241* (2013.01); *A61B 5/02416* (2013.01); *A61B 5/031* (2013.01); *A61B 5/14551* (2013.01); *A61B 5/318* (2021.01); *A61B 5/369* (2021.01); *A61B 5/398* (2021.01); *A61B 5/4836* (2013.01); *A61B 5/6826* (2013.01); *A61B 5/7246* (2013.01); *A61B 5/7267* (2013.01); *A61B 5/742* (2013.01); *A61B 7/04* (2013.01); *A61B 2562/0219* (2013.01); *A61M 1/1613* (2014.02); *G16H 20/17* (2018.01); *G16H 20/30* (2018.01)

(56) References Cited

U.S. PATENT DOCUMENTS

| | | | |
|---|---|---|---|
| 5,619,990 A * | 4/1997 | Kanai | G16H 50/30 600/300 |
| 5,853,364 A | 12/1998 | Baker, Jr. et al. | |
| 5,865,168 A | 2/1999 | Isaza | |
| 5,967,981 A | 10/1999 | Watrous | |
| 5,984,893 A | 11/1999 | Ward | |
| 6,083,172 A | 7/2000 | Baker, Jr. et al. | |
| 6,094,592 A | 7/2000 | Yorkey et al. | |
| 6,206,830 B1 | 3/2001 | Diab et al. | |
| 6,248,080 B1 | 6/2001 | Miesel | |
| 6,338,713 B1 | 1/2002 | Chamoun et al. | |
| 6,371,921 B1 | 4/2002 | Caro et al. | |
| 6,398,728 B1 | 6/2002 | Bardy | |
| 6,409,675 B1 | 6/2002 | Turcott | |
| 6,411,833 B1 | 6/2002 | Baker, Jr. et al. | |
| 6,553,991 B1 | 4/2003 | Isaza | |
| 6,556,852 B1 | 4/2003 | Schulze | |
| 6,557,553 B1 | 5/2003 | Borrello | |
| 6,558,336 B2 | 5/2003 | Collins | |
| 6,589,189 B2 | 7/2003 | Meyerson et al. | |
| 6,591,122 B2 | 7/2003 | Schmitt | |
| 6,606,509 B2 | 8/2003 | Schmitt | |
| 6,675,031 B1 | 1/2004 | Porges et al. | |
| 6,721,584 B2 | 4/2004 | Baker, Jr. et al. | |
| 6,739,337 B2 | 5/2004 | Isaza | |
| 6,852,083 B2 | 2/2005 | Caro et al. | |
| 7,160,250 B2 | 1/2007 | Lemaire | |
| 7,231,245 B2 | 6/2007 | Greenwald et al. | |
| 7,285,100 B2 | 10/2007 | Lemaire | |
| 7,455,643 B1 | 11/2008 | Li et al. | |
| 7,547,283 B2 | 6/2009 | Mourad et al. | |
| 7,496,393 B2 | 11/2009 | Diab et al. | |
| 7,647,185 B2 | 1/2010 | Tarassenko et al. | |
| 7,654,964 B1 | 2/2010 | Kroll et al. | |
| 7,668,579 B2 | 2/2010 | Lynn | |
| 7,678,507 B2 | 3/2010 | Berkow et al. | |
| 7,720,516 B2 | 5/2010 | Chin et al. | |
| 7,865,224 B2 | 1/2011 | Baker, Jr. et al. | |
| 7,873,497 B2 | 1/2011 | Weber et al. | |
| 7,887,502 B2 | 2/2011 | Ross et al. | |
| 7,931,559 B2 | 4/2011 | Baker, Jr. et al. | |
| 7,957,780 B2 | 6/2011 | Lamego et al. | |
| 7,976,472 B2 | 7/2011 | Kiani | |
| 8,019,400 B2 | 9/2011 | Diab et al. | |
| 8,463,346 B2 | 6/2013 | Kuhn et al. | |
| 8,512,260 B2 | 8/2013 | Grudic et al. | |
| 8,641,635 B2 | 2/2014 | Melker et al. | |
| 9,603,534 B2 | 3/2017 | Gabbay et al. | |
| 9,757,041 B2 | 9/2017 | Grudic et al. | |
| 10,226,194 B2 | 3/2019 | Grudic et al. | |
| 2001/0027335 A1 | 10/2001 | Meyerson et al. | |
| 2003/0060690 A1 | 3/2003 | Jelliffe et al. | |
| 2003/0125612 A1 | 7/2003 | Fox et al. | |
| 2003/0130570 A1 | 7/2003 | Krivitski et al. | |
| 2003/0176931 A1 | 9/2003 | Pednault et al. | |
| 2003/0200189 A1 | 10/2003 | Meng et al. | |
| 2003/0212678 A1 | 11/2003 | Bloom et al. | |
| 2004/0215244 A1 | 10/2004 | Marcovecchio et al. | |
| 2004/0242972 A1 | 12/2004 | Adak et al. | |
| 2004/0267145 A1 * | 12/2004 | David | A61B 5/02055 600/509 |
| 2005/0015009 A1 | 1/2005 | Mourad et al. | |
| 2005/0209516 A1 | 9/2005 | Fraden | |
| 2005/0228298 A1 | 10/2005 | Banet et al. | |
| 2006/0058691 A1 | 3/2006 | Kiani | |
| 2006/0106743 A1 | 5/2006 | Horvitz | |
| 2006/0161403 A1 | 7/2006 | Jiang et al. | |
| 2006/0166176 A1 | 7/2006 | Lakin et al. | |
| 2006/0178585 A1 | 8/2006 | Sharrock | |
| 2006/0195041 A1 | 8/2006 | Lynn et al. | |

(56) References Cited

U.S. PATENT DOCUMENTS

| | | |
|---|---|---|
| 2006/0253016 A1 | 11/2006 | Baker, Jr. et al. |
| 2007/0015972 A1 | 1/2007 | Wang et al. |
| 2007/0032732 A1 | 2/2007 | Shelley et al. |
| 2007/0099239 A1 | 5/2007 | Tabibiazar et al. |
| 2007/0112275 A1 | 5/2007 | Cooke et al. |
| 2007/0213619 A1* | 9/2007 | Linder ............... A61B 5/02416 600/481 |
| 2008/0039731 A1 | 2/2008 | McCombie et al. |
| 2008/0045845 A1 | 2/2008 | Pfeiffer et al. |
| 2008/0067132 A1 | 3/2008 | Ross et al. |
| 2008/0077023 A1 | 3/2008 | Campbell et al. |
| 2008/0097173 A1 | 4/2008 | Soyemi et al. |
| 2008/0133434 A1 | 6/2008 | Asar et al. |
| 2008/0146890 A1 | 6/2008 | LeBoeuf et al. |
| 2008/0146892 A1 | 6/2008 | LeBoeuf et al. |
| 2008/0154814 A1 | 6/2008 | Chaudhury et al. |
| 2008/0234607 A1 | 9/2008 | Hunter-Jones et al. |
| 2008/0294217 A1 | 11/2008 | Lian et al. |
| 2009/0005703 A1 | 1/2009 | Fasciano |
| 2009/0036754 A1 | 2/2009 | Pons et al. |
| 2009/0069647 A1 | 3/2009 | McNames et al. |
| 2009/0112106 A1 | 3/2009 | Zhang |
| 2009/0143656 A1 | 6/2009 | Manwaring et al. |
| 2009/0149724 A1 | 6/2009 | Mark et al. |
| 2009/0149751 A1 | 6/2009 | Mourad et al. |
| 2009/0204162 A1 | 8/2009 | Addison et al. |
| 2009/0264776 A1 | 10/2009 | Vardy |
| 2009/0272678 A1 | 11/2009 | Sornmo et al. |
| 2009/0281434 A1* | 11/2009 | Messerges ............... A61B 5/02 600/485 |
| 2009/0287105 A1 | 11/2009 | Hirsch |
| 2009/0292198 A1 | 11/2009 | Kleiven et al. |
| 2009/0043222 A1 | 12/2009 | Chetham |
| 2010/0016739 A1 | 1/2010 | Shelley et al. |
| 2010/0041962 A1 | 2/2010 | Causevic et al. |
| 2010/0081942 A1* | 4/2010 | Huiku ................ G06F 19/00 600/483 |
| 2010/0094158 A1 | 4/2010 | Solem et al. |
| 2010/0160795 A1 | 6/2010 | Banet et al. |
| 2010/0191128 A1 | 7/2010 | Shelley et al. |
| 2010/0204589 A1 | 8/2010 | Swoboda et al. |
| 2010/0249559 A1 | 9/2010 | Lovejoy |
| 2011/0077532 A1 | 3/2011 | Kim et al. |
| 2011/0112799 A1 | 5/2011 | Weber et al. |
| 2011/0152651 A1 | 6/2011 | Berkow |
| 2011/0160549 A1 | 6/2011 | Saroka et al. |
| 2011/0172545 A1 | 7/2011 | Grudic et al. |
| 2011/0201962 A1 | 8/2011 | Grudic et al. |
| 2011/0282169 A1 | 8/2011 | Grudic et al. |
| 2011/0237914 A1 | 9/2011 | Lamego et al. |
| 2012/0123232 A1 | 5/2012 | Najarian et al. |
| 2012/0136224 A1 | 5/2012 | Najarian et al. |
| 2012/0184840 A1 | 7/2012 | Najarian et al. |
| 2012/0245439 A1 | 9/2012 | André et al. |
| 2012/0269420 A1 | 10/2012 | Najarian et al. |
| 2012/0296219 A1 | 11/2012 | Chon et al. |
| 2012/0330117 A1 | 12/2012 | Grudic et al. |
| 2013/0041268 A1 | 2/2013 | Rimoldi et al. |
| 2013/0218056 A1 | 8/2013 | Aelen et al. |
| 2013/0245397 A1 | 9/2013 | Grudic et al. |
| 2013/0261468 A1 | 10/2013 | Semler et al. |
| 2013/0343585 A1 | 12/2013 | Bennett et al. |
| 2014/0073938 A1 | 3/2014 | Rodriguez-Llorente et al. |
| 2014/0107437 A1 | 4/2014 | Pinsky |
| 2014/0236053 A1 | 8/2014 | Walker et al. |
| 2015/0065826 A1 | 3/2015 | Mulligan et al. |
| 2015/0073723 A1 | 3/2015 | Mulligan et al. |
| 2015/0141769 A1 | 5/2015 | Mulligan et al. |
| 2016/0015284 A1 | 1/2016 | Grudic et al. |
| 2016/0038042 A1 | 2/2016 | Mulligan et al. |
| 2016/0038043 A1 | 2/2016 | Mulligan et al. |
| 2016/0162786 A1 | 6/2016 | Grudic et al. |
| 2016/0354039 A1 | 12/2016 | Soto et al. |
| 2017/0007139 A9 | 1/2017 | Grudic et al. |
| 2017/0215016 A1 | 7/2017 | Dohmen et al. |
| 2017/0258329 A1 | 9/2017 | Marsh |
| 2017/0303799 A1 | 10/2017 | Grudic et al. |
| 2017/0347177 A1 | 11/2017 | Masaki |
| 2018/0214028 A1 | 8/2018 | Zhang et al. |
| 2020/0205734 A1 | 7/2020 | Mulligan et al. |
| 2020/0205747 A1 | 7/2020 | Mulligan et al. |

FOREIGN PATENT DOCUMENTS

| | | |
|---|---|---|
| WO | WO 2003-077854 A2 | 9/2003 |
| WO | WO 2003-091421 A3 | 11/2003 |
| WO | WO-2005-055825 A1 | 6/2005 |
| WO | WO-2005-112756 A1 | 12/2005 |
| WO | WO-2007-011565 A1 | 1/2007 |
| WO | WO 2007-098957 A1 | 9/2007 |
| WO | WO 2007-117570 A2 | 10/2007 |
| WO | WO 2007-149533 A2 | 12/2007 |
| WO | WO 2010-009735 A2 | 1/2010 |
| WO | WO 2010-053743 A1 | 5/2010 |
| WO | WO 2010-117572 A2 | 10/2010 |
| WO | WO-2011-002904 A2 | 1/2011 |
| WO | WO 2011-050066 A2 | 4/2011 |
| WO | WO 2011-103102 A1 | 8/2011 |
| WO | WO 2011-109734 A1 | 9/2011 |
| WO | WO 2012-054880 A2 | 4/2012 |
| WO | WO 2012-166568 A3 | 12/2012 |
| WO | WO 2013-016212 A1 | 1/2013 |
| WO | WO 2014-149981 A1 | 9/2014 |
| WO | WO-2015-042484 A1 | 3/2015 |
| WO | WO 2015-069940 A1 | 5/2015 |
| WO | WO 2015-073909 A1 | 5/2015 |
| WO | WO 2015-073910 A1 | 5/2015 |
| WO | WO 2016-061542 A1 | 4/2016 |
| WO | WO 2016-061545 A1 | 4/2016 |
| WO | WO-2017-044868 A1 | 3/2017 |
| WO | WO-2017-218431 A1 | 12/2017 |

OTHER PUBLICATIONS

U.S. Appl. No. 14/535,171, NonFinalOA dated Dec. 16, 2016, 37 pages.

U.S. Appl. No. 14/885,888, NonFinalOA dated Dec. 16, 2016, 35 pages.

Nadler et al. 2014, Shock 42(2): 93-98, "The Value of Noninvasive Measurement of the Compensatory Reserve Index in Monitoring and Triage of Patients Experiencing Minimal Blood Loss".

Nadler et al. 2017, Annals of Medicine and Surgery, "The approximated cardiovascular reserve index complies with haemorrhage related hemodynamic deterioration pattern: A swine exsanguination model" 7 pages.

Canadian Patent Application No. 2,775,675, NonFinalOA dated Nov. 9, 2016; 4 pages.

U.S. Appl. No. 13/041,006, NonFinalOA dated Mar. 7, 2017, 21 pages.

U.S. Appl. No. 13/554,483, Notice of Allowance dated Mar. 7, 2017, 39 pages.

International Search Report and Written Opinion prepared by the U.S. Patent and Trademark Office as International Searching Authority for PCT International Patent Application No. PCT/US09/62119, dated Feb. 3, 2010, 5 pages.

International Preliminary Report on Patentability prepared by the International Bureau for PCT/US2009/062119, dated May 12, 2011, 6 pages.

Decision to Grant, dated Apr. 23, 2015 for EP 09825222.4, 3 pages.
European Search Report, dated Jun. 15, 2012 for EP 09825222.4, 10 pages.

Procopio et al (2008) Intelligent Robots And Systems IEEE/RSJ International Conference, pp. 620-627, "Learning in 1-14 dynamic environments with Ensemble Selection for autonomous outdoor robot navigation".

Shoemaker, et al (2001) CHEST, 120(2):528-538, "Outcome Prediction of Emergency Patients by Noninvasive Hemodynamic Monitoring".

Supplemental European Search Report, dated Jul. 3, 2012 for EP 09825222.4, 1 page.

(56) References Cited

OTHER PUBLICATIONS

U.S. Appl. No. 13/126,727, NonFinal Office Action dated Sep. 11, 2014; 58 pages.
U.S. Appl. No. 13/028,140, NonFinal Office Action dated Nov. 13, 2012; 27 pages.
U.S. Appl. No. 13/028,140, Notice of Allowance dated Feb. 22, 2013; 22 pages.
U.S. Appl. No. 13/028,140, Restriction Requirement dated Aug. 1, 2012; 7 pages.
U.S. Appl. No. 13/889,513, NonFinal Office Action dated Jun. 15, 2015, 27 pages.
International Preliminary Report on Patentability prepared by the International Bureau for PCT/US11/24938, dated Aug. 30, 2012, 7 pages.
International Search Report and Written Opinion prepared by the U.S. Patent and Trademark Office as International Searching Authority for PCT International Patent Application No. PCT/US2011/24938, dated Jun. 7, 2011, 13 pages.
Supplemental European Search Report, dated Jun. 21, 2013 for EP 11745124.5, 7 pages.
U.S. Appl. No. 13/041,006, NonFinal Office Action dated May 23, 2014; 27 pages.
U.S. Appl. No. 13/041,006, NonFinal Office Action dated Dec. 22, 2014; 14 pages.
International Preliminary Report on Patentability prepared by the International Bureau for PCT/US11/27237, dated Sep. 13, 2012, 10 pages.
International Search Report and Written Opinion prepared by the U.S. Patent and Trademark Office as International Searching Authority for PCT International Patent Application No. PCT/US2011/027237, dated May 27, 2011, 16 pages.
Cooke et al. (2004) Journal of Applied Physiology 96(4):1249-1261, "Lower body negative pressure as a model to study progression to acute hemorrhagic shock in humans".
Extended European Search Report, dated Oct. 18, 2013 for EP11751440.6, 7 pages.
Lambert et al. (2007) ACTA Anaesthesiologica Scandinavica 51(4):415-425, "Does a positive 1-27 end-expiratory pressure-induced reduction in stroke volume indicate preload responsiveness? An experimental study".
Ryan et al. (2008) Journal of Applied Physiology 104(5):1402-1409, "Breathing through an inspiratory threshold device improves stroke volume during central hypovolemia in humans".
Supplemental Extended European Search Report, dated Nov. 6, 2013 for EP11751440.6, 8 pages.
International Preliminary Report on Patentability prepared by the International Bureau for PCT International Patent Application No. PCT/US12/047659, dated Feb. 6, 2014, 10 pages.
International Search Report and Written Opinion prepared by the U.S. Patent and Trademark Office as International Searching Authority for PCT International Patent Application No. PCT/US12/47659, dated Oct. 12, 2012, 16 pages.
Extended European Search Report for EP 12816832.5, dated Oct. 6, 2014, 9 pages.
International Search Report and Written Opinion prepared by the Korean Intellectual Property Office as International Searching Authority for PCT International Patent Application No. PCT/US2014/064413, dated Feb. 12, 2015, 13 pages.
International Search Report and Written Opinion prepared by the Korean Intellectual Property Office as International Searching Authority for PCT International Patent Application No. PCT/US2014/065818, dated Feb. 26, 2015, 14 pages.
International Search Report and Written Opinion prepared by the Korean Intellectual Property Office as International Searching Authority for PCT International Patent Application No. PCT/US2014/065820, dated Feb. 26, 2015, 14 pages.
Berkow (Aug. 2010) Intelomed, Inc., "CVInsight," 14 pages.
Berkow (Jan. 2012) 510(K) Summary, "CVInsight," 9 pages.
Najarian (2012) VCU School of Engineering ResearchReport, vol. 5, p. 3.

U.S. Appl. No. 13/126,727, Final Rejection dated Aug. 27, 2015; 33 pages.
U.S. Appl. No. 13/041,006, Final Rejection dated Sep. 15, 2015; 19 pages.
Canadian Patent Application No. 2,775,675, NonFinalOA dated Dec. 9, 2015; 3 pages.
International Search Report and Written Opinion prepared by the Korean Intellectual Property Office as International Searching Authority for PCT International Patent Application No. PCT/US2015/056078, dated Jan. 25, 2016, 11 pages.
International Search Report and Written Opinion prepared by the Korean Intellectual Property Office as International Searching Authority for PCT International Patent Application No. PCT/US2015/56074, dated Jan. 29, 2016, 13 pages.
Convertino, Victor, "Estimation of individual-specific progression to impending cardiovascular instability using arterial waveforms," Journal of Applied Physiology, Oct. 15, 2013, vol. 115, No. 8, pp. 1196-1202.
U.S. Appl. No. 14/542,426,Non-Final Office Action dated Feb. 26, 2016; 25 pages.
U.S. Appl. No. 13/554,483, Non-Final Office Action dated Mar. 22, 2016; 41 pages.
EP11751440.6, Office Action 94(3) dated Feb. 24, 2016, 5 pages.
U.S. Appl. No. 13/041,006, Non-final Office Action dated Apr. 22, 2016, 15 pages.
International Preliminary Report on Patentability prepared by the International Bureau for PCT International Patent Application No. PCT/US14/064413, dated May 19, 2016, 10 pages.
International Preliminary Report on Patentability prepared by the International Bureau for PCT International Patent Application No. PCT/US14/65818, dated May 26, 2016, 11 pages.
International Preliminary Report on Patentability prepared by the International Bureau for PCT International Patent Application No. PCT/US14/65820, dated May 26, 2016, 11 pages.
Stewart et al. (2016) PubMed Epub ahead of print, "The Compensatory Reserve Index Following Injury: Results of a Prospective Clinical Trial" 2 pages.
U.S. Appl. No. 14/542,426, Final Office Action dated Sep. 26, 2016, 25 pages.
Intravenous Therapy (Wikipedia) Accessed on: Sep. 27, 2016, 12 pages.
U.S. Appl. No. 13/554,483, Final Office Action dated Oct. 7, 2016, 28 pages.
U.S. Appl. No. 13/889,513, Final Rejection dated Apr. 11, 2017; 51 pages.
Schmidt et al. (1997) Stroke, "Noninvasive Prediction of Intracranial Pressure Curves Using Transcranial Doppler Ultrasonography and Blood Pressure Curves," 22 pages.
International Preliminary Report on Patentability prepared by the International Bureau for PCT/US15/56074, dated Apr. 27, 2017, 10 pages.
International Preliminary Report on Patentability prepared by the International Bureau for PCT/US15/56078, dated Apr. 27, 2017, 7 pages.
U.S. Appl. No. 14/542,426,Non-Final Office Action dated May 5, 2017; 17 pages.
U.S. Appl. No. 14/542,423, Non-Final Office Action dated May 8, 2017; 35 pages.
U.S. Appl. No. 14/885,891, Non-Final OA dated May 18, 2017; 29 pages.
Extended European Search Report for EP14862697.1, dated Jun. 14, 2017; 8 pages.
U.S. Appl. No. 14/885,888, Final Office Action dated Jul. 27, 2017, 29 pages.
EP 11745124.5, Office Action 94(3) dated Jul. 31, 2017, 6 pages.
Kotsiantis (2007) Department of Computer Science and Technology, "Supervised Machine Learning: A Review of Classification Techniques," 20 pages.
Wu et al, (2009) World Congress on Computer Science and Information Engineering, "Time Series Mining Approach for Noninvasive Intracranial Pressure Assessment: An Investigation of Different Regularization Techniques," 5 pages.

(56) References Cited

OTHER PUBLICATIONS

Extended European Search Report, dated Jun. 7, 2017 for EP14862921.5, 8 pages.
Extended European Search Report, dated Jun. 20, 2017 for EP14859538.2, 8 pages.
International Search Report and Written Opinion prepared by the Korean Intellectual Property Office as International Searching Authority for PCT International Patent Application No. PCT/US2017/037067, dated Aug. 18, 2017, 21 pages.
U.S. Appl. No. 14/535,171, Final Office Action dated Nov. 16, 2017, 30 pages.
U.S. Appl. No. 13/889,513, NonFinal Office Action dated Dec. 1, 2017, 51 pages.
U.S. Appl. No. 14/867,938, NonFinal Office Action dated Dec. 8, 2017, 27 pages.
U.S. Appl. No. 13/041,006, NonFinal Office Action dated Dec. 15, 2017, 21 pages.
Canadian Patent Application No. 2,775,675, NonFinalOA dated Sep. 27, 2017; 4 pages.
U.S. Appl. No. 14/542,426, Non-Final Office Action dated Feb. 1, 2018, 19 pages.
U.S. Appl. No. 14/542,423, NonFinal Office Action dated Feb. 5, 2018, 24 pages.
U.S. Appl. No. 14/885,891, NonFinalOA dated Feb. 5, 2018, 22 pages.
Canadian Patent Application No. 2,871,608, NonFinalOA dated Jan. 25, 2018; 5 pages.
U.S. Appl. No. 14/885,888, NonFinal Office Action dated Mar. 15, 2018, 11 pages.
International Preliminary Report on Patentability prepared by the International Bureau for PCT/US2009/062119, dated Mar. 22, 2018, 9 pages.
U.S. Appl. No. 15/649,411, NonFinalOA dated Apr. 5, 2018, 23 pages.
Extended European Search Report for EP15850241.9, dated Apr. 5, 2018; 8 pages.
U.S. Appl. No. 15/007,489, NonFinal Office Action dated Jun. 13, 2018; 48 pages.
U.S. Appl. No. 14/535,171, NonFinalOA dated Aug. 9, 2018, 23 pages.
U.S. Appl. No. 14/867,938, Notice of Allowance dated Sep. 6, 2018; 17 pages.
U.S. Appl. No. 13/889,513, Final Office Action dated Sep. 20, 2018, 25 pages.
U.S. Appl. No. 14/542,426, Final Office Action dated Sep. 27, 2018, 11 pages.
U.S. Appl. No. 14/885,888, Final Office Action dated Sep. 28, 2018, 7 pages.
U.S. Appl. No. 14/885,891, Final Office Action dated Sep. 28, 2018, 10 pages.
U.S. Appl. No. 13/041,006, Final Office Action dated Oct. 3, 2018, 9 pages.
Canadian Patent Application No. 2,871,608, NonFinalOA dated Nov. 22, 2018, 3 pages.
European Patent Application No. 12816832.5, NonFinalOA dated Oct. 12, 2018, 4 pages.
International Preliminary Report on Patentability prepared by the International Bureau for PCT International Patent Application No. PCT/US2017/037067, dated Dec. 27, 2018, 13 pages.
U.S. Appl. No. 14/542,423, NonFinal Office Action dated Dec. 28, 2018, 18 pages.
Extended European Search Report for EP16845202.7, dated Feb. 1, 2019, 6 pages.
Moulton et al. (2013) Trauma Acute Care Surg 75(6): 1053-1059, "Running on empty? The Compensatory Reserve Index".
Poh et al. (2014) Experimental Physiology, 1421-1426, "Respiratory Pump Contributes to Increased Physiological Reserve for Compensation During Simulated Haemorrhage".
EPO Communication pursuant to Rules 161(2) and 162 EPC dated Feb. 1, 2019, 4 pages.
Extended European Search Report Written Opinion for EP16845202.7, dated Mar. 11, 2019, 8 pages.
EPO Communication pursuant to Rule 70(2) and 70(a)(2) EPC, dated Mar. 13, 2019, 1 page.
U.S. Appl. No. 15/007,489, Final Office Action dated Mar. 20, 2019, 36 pages.
U.S. Appl. No. 15/649,411, NonFinalOA dated Apr. 2, 2019, 24 pages.
U.S. Appl. No. 13/041,006, NonFinalOA dated Apr. 4, 2019, 15 pages.
U.S. Appl. No. 14/542,426, NonFinalOA dated Apr. 5, 2019, 9 pages.
U.S. Appl. No. 13/889,513, Restriction Requirement dated Apr. 12, 2019, 9 pages.
U.S. Appl. No. 14/885,888, Non-Final Office Action dated May 15, 2019, 21 pages.
U.S. Appl. No. 14/885,891, Non-Final Office Action dated May 15, 2019, 18 pages.
U.S. Appl. No. 14/535,171, FinalOA dated Jul. 3, 2019, 20 pages.
U.S. Appl. No. 14/542,423, NonFinal Office Action dated Jul. 9, 2019, 17 pages.
U.S. Appl. No. 15/620,701, NonFinal Office Action dated Aug. 12, 2019, 27 pages.
Japan Patent Application No. 2017-539521 Office Action, dated Sep. 5, 2019, 7 pages.
EP Application No. 15850241.9, EP Examination Report, dated Oct. 14, 2019, 6 pages.
U.S. Appl. No. 16/726,334, filed Dec. 24, 2019 by Mulligan et al. and entitled "Device-Based Maneuver and Activity State-Based Physiologic Status Monitoring," 89 pages.
U.S. Appl. No. 16/726,337, filed Dec. 24, 2019 by Mulligan et al. and entitled "Ear-Based Physiological State Monitoring" 78 pages.
U.S. Appl. No. 15/649,411, Final OA dated Dec. 23, 2019, 19 pages.
U.S. Appl. No. 14/885,888, Final Office Action dated Jan. 2, 2020, 2019, 21 pages.
U.S. Appl. No. 14/542,426, Final OA dated Dec. 20, 2019, 19 pages.
U.S. Appl. No. 14/535,171, Non-Final Rejection dated Jan. 23, 2020, 20 pages.
U.S. Appl. No. 13/041,006, Final Rejection dated Jan. 27, 2020; 10 pages.
U.S. Appl. No. 13/889,513, Non-Final OA, dated Jan. 28, 2020, 27 pages.
U.S. Appl. No. 14/885,891, Final Office Action dated Mar. 3, 2020, 19 pages.
U.S. Appl. No. 13/041,006, Final Rejection, dated Jan. 7, 2021; 30 pages.
U.S. Appl. No. 14/885,888, Final Office Action dated Mar. 30, 2021, 25 pages.
U.S. Appl. No. 13/889,513, Notice of Abandonment, dated Sep. 25, 2020, 2 pages.
U.S. Appl. No. 14/535,171, Non-Final Office Action dated Oct. 5, 2020, 21 pages.
U.S. Appl. No. 14/542,423, Non-Final Office Action dated Oct. 6, 2020, 21 pages.
U.S. Appl. No. 15/620,701, Non-Final Office Action dated Oct. 21, 2020, 20 pages.
U.S. Appl. No. 14/542,423, Final Office Action dated May 18, 2020, 21 pages.
U.S. Appl. No. 13/041,006, Non-Final Rejection dated Jun. 12, 2020; 29 pages.
U.S. Appl. No. 15/620,701, Final Office Action dated Jun. 22, 2020, 25 pages.
EPO Communication pursuant to Rules 71(3) dated Jun. 23, 2020, 57 pages.
U.S. Appl. No. 15/649,411, Non-Final Office Action, dated Jul. 29, 11 pages.
U.S. Appl. No. 14/885,891, Non-Final Office Action dated Aug. 6, 2020, 19 pages.
U.S. Appl. No. 14/885,888, Non-Final Office Action dated Aug. 6, 2020, 2019, 21 pages.
U.S. Appl. No. 14/542,426, Non-Final Office Action dated Aug. 6, 2020, 2019, 19 pages.

(56) References Cited

OTHER PUBLICATIONS

U.S. Appl. No. 16/726,337, Final Office Action dated Sep. 7, 2021, 68 pages.
U.S. Appl. No. 15/620,701, Final Office Action dated Oct. 26, 2021, 22 pages.
U.S. Appl. No. 16/726,337, Non-Final Office Action dated May 17, 2021; 79 pages.
U.S. Appl. No. 14/535,171, Final Office Action dated May 19, 2021, 22 pages.
U.S. Appl. No. 14/542,423, Final Office Action dated May 19, 2021, 21 pages.
U.S. Appl. No. 15/649,411, Non-Final Office Action, dated May 19, 2021, 21 pages.
U.S. Appl. No. 14/542,426, Final Office Action dated Jun. 1, 2021, 20 pages.
U.S. Appl. No. 15/620,701, Non-Final Office Action dated Jun. 6, 2021, 22 pages.
U.S. Appl. No. 14/885,891, Non-Final Office Action, dated Jun. 8, 2021, 23 pages.
U.S. Appl. No. 13/041,006, Non-Final Office Action dated Jul. 16, 2021; 32 pages.
U.S. Appl. No. 14/885,888, Non-Final Office Action, dated Dec. 24, 2021, 28 pages.
U.S. Appl. No. 14/885,891, Final Office Action, dated Dec. 24, 2021, 24 pages.
U.S. Appl. No. 13/041,006, Final Office Action, dated Jan. 27, 2022; 32 pages.
U.S. Appl. No. 15/649,411, Notice of Allowance, dated Feb. 2, 2022, 30 pages.
U.S. Appl. No. 14/535,171, Notice of Allowance, dated Feb. 9, 2022, 30 pages.
U.S. Appl. No. 14/542,423, Notice of Allowance, dated Mar. 16, 2022; 29 pages.

* cited by examiner

1200

ESTIMATING PHYSIOLOGICAL STATES BASED ON CHANGES IN CRI

CROSS-REFERENCE TO RELATED APPLICATIONS

This application claims the benefit, under 35 U.S.C. § 119(e), of the following provisional applications: provisional U.S. Patent Application No. 62/349,516, filed Jun. 13, 2016 by Mulligan et al. and entitled "Rapid Detection of Bleeding Following Injury", referred to herein as the "'516 application", and provisional U.S. Patent Application No. 62/216,187, filed Sep. 9, 2015 by Mulligan et al. and entitled "Estimating Physiological States Based on Changes in CRI", referred to herein as the "'187 application", both of which are incorporated herein by reference in their entirety.

This application is also a continuation-in-part application of U.S. patent application Ser. No. 14/885,891, filed Oct. 16, 2015 by Mulligan et al. and entitled "Assessing Effectiveness of CPR", referred to herein as the "'891 application", which is incorporated herein by reference in its entirety. This application is also a continuation-in-part application of U.S. patent application Ser. No. 14/885,888, filed Oct. 16, 2015 by Mulligan et al. and entitled "Rapid Detection of Bleeding Before, During, and After Fluid Resuscitation", referred to herein as the "'888 application", which is incorporated herein by reference in its entirety and which claims priority to provisional U.S. Patent Application No. 62/064,816, filed Oct. 16, 2014 by Mulligan et al. and titled "Assessing the Effectiveness of CPR" and provisional U.S. Patent Application No. 62/064,809 filed Oct. 16, 2014 by Mulligan et al. and titled "Rapid Detection of Bleeding During Fluid Resuscitation", each of which are incorporated herein by reference in their entirety.

The '888 application is a continuation-in-part application of U.S. patent application Ser. No. 14/542,426, filed Nov. 14, 2014 by Mulligan et al. and titled, "Noninvasive Hydration Monitoring", referred to herein as the "'426 application", which is incorporated herein by reference in its entirety. The '888 Application is also a continuation-in-part application of U.S. patent application Ser. No. 14/542,423, filed Nov. 14, 2014 by Mulligan et al. and titled, "Noninvasive Monitoring for Fluid Resuscitation", referred to herein as the "'423 application", which is incorporated herein by reference in its entirety and which claims priority to provisional U.S. Patent Application No. 61/905,727, filed Nov. 18, 2013 by Mulligan et al. and titled "Noninvasive Hydration Monitoring", referred to herein as the "'436 application" and provisional U.S. Patent Application No. 61/904,436, filed Nov. 14, 2013 by Mulligan et al. and titled "Noninvasive Monitoring for Fluid Resuscitation", referred to herein as the "'436 application", each of which are incorporated herein by reference in their entirety.

The '423 application is a continuation-in-part application of U.S. patent application Ser. No. 14/535,171, filed Nov. 6, 2014 by Mulligan et al. and titled "Noninvasive Predictive and/or Estimative Blood Pressure Monitoring", referred to herein as the "'171 application", which is incorporated herein by reference in its entirety and which claims priority to provisional U.S. Patent Application No. 61/900,980, filed Nov. 6, 2013 by Mulligan et al. and titled "Noninvasive Predictive and/or Estimative Blood Pressure Monitoring", which is incorporated herein by reference in its entirety.

The '171 application is a continuation-in-part application of U.S. patent application Ser. No. 13/554,483, filed Jul. 20, 2012 by Grudic et al. and titled, "Hemodynamic Reserve Monitor and Hemodialysis Control", referred to herein as the "'483 application", which is hereby incorporated by reference in its entirety and which claims priority to provisional U.S. Patent Application No. 61/510,792, filed Jul. 22, 2011 by Grudic et al. and entitled "Cardiovascular Reserve Monitor" and provisional U.S. Patent Application No. 61/614,426, filed Mar. 22, 2012 by Grudic et al. and entitled "Hemodynamic Reserve Monitor and Hemodialysis Control", both of which are hereby incorporated by reference in its entirety.

The '483 application is a continuation-in-part application of U.S. patent application Ser. No. 13/041,006, filed Mar. 4, 2011 by Grudic et al. and entitled "Active Physical Perturbations to Enhance Intelligent Medical Monitoring", referred to herein as the "'006 application", which is hereby incorporated by reference in its entirety and which claims priority to provisional U.S. Patent Application No. 61/310,583, filed Mar. 4, 2010 by Grudic et al. and titled "Active Physical Perturbations to Enhance Intelligent Medical Monitoring", which is hereby incorporated by reference in its entirety.

The '006 application is a continuation-in-part application of U.S. patent application Ser. No. 13/028,140, filed Feb. 15, 2011 by Grudic et al. and entitled "Statistical, Noninvasive Measurement of Intracranial Pressure", referred to herein as the "'140 application"; now issued U.S. Pat. No. 8,512,260, which is hereby incorporated by reference in its entirety and which claims priority to provisional U.S. Patent Application No. 61/305,110, filed Feb. 16, 2010, by Moulton et al. and titled "Statistical, Noninvasive Method for Measuring Intracranial Pressure", which is hereby incorporated by reference in its entirety.

The '140 application is a continuation-in-part application of International Application No. PCT/US2009/062119, filed Oct. 26, 2009 by Grudic et al. and entitled "Long Term Active Learning from Large Continually Changing Data Sets", which is hereby incorporated by reference in its entirety and which claims priority to provisional U.S. Patent Application No. 61/252,978 filed Oct. 19, 2009 by Grudic et al. and titled "Long Term Active Learning from Large Continually Changing Data Sets," provisional U.S. Patent Application No. 61/166,499, filed Apr. 3, 2009 by Moulton and titled "Advances in Pre-Hospital Care," provisional U.S. Patent Application No. 61/166,486, filed Apr. 3, 2009 by Grudic et al. and titled "Statistical Methods for Predicting Patient Specific Blood Loss Volume Causing Hemodynamic Decompensation," provisional U.S. Patent Application No. 61/166,472, filed Apr. 3, 2009 by Grudic et al. and titled "Long Term Active Learning from Large Continually Changing Data Sets," and provisional U.S. Patent Application No. 61/109,490, filed Oct. 29, 2008 by Moulton et al. and titled "Method for Determining Physiological State or Condition," each of which is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under grant number 0535269 awarded by the National Science Foundation; grant number FA8650-07-C-7702 awarded by the Air Force Research Laboratory; and grant numbers W81XWH-09-C-1060 and W81XWH-09-1-0750 awarded by Army Medical Research Material and Command. The government has certain rights in the invention.

The respective disclosures of these applications/patents (collectively, the "Related Applications" are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BRIEF SUMMARY

Various embodiments can assess the physiological state of a patient, perhaps indicated by changes in a patient's compensatory reserve index ("CRI," also referred to herein and in the Related Applications as "cardiac reserve index" or "hemodynamic reserve index" ("HDRI"), all of which should be considered synonymous for purposes of this disclosure) in response to a physical perturbation. (While the term, "patient," is used herein for convenience, that descriptor should not be considered limiting, because various embodiments can be employed both in a clinical setting and outside any clinical setting, such as by an athlete before, during, or after an athletic contest or training, a person during daily activities, a soldier on the battlefield, etc. Thus, the term, "patient," as used herein, should be interpreted broadly and should be considered to be synonymous with "person.") In other cases, the assessments might be based on raw waveform data (e.g., PPG waveform data) captured by a sensor on the patent (such as the sensors described below and in the Related Applications, for example). In further cases, a combination of waveform data and calculated/estimated CRI can be used to calculate the effectiveness of hydration and/or the amount of fluid needed for effective hydration. In other aspects, such functionality can be provided by and/or integrated with systems, devices (such as a cardiac reserve monitor and/or wrist-worn sensor device), tools, techniques, methods, and software described below and in the Related Applications.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Figure 1A:
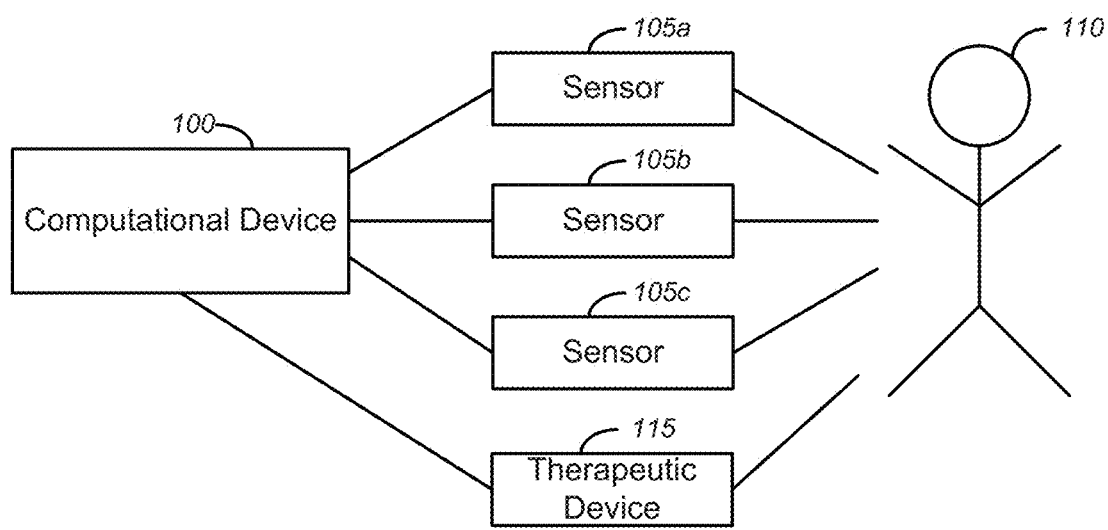
FIG. 1A is a schematic diagram illustrating a system for estimating compensatory reserve, in accordance with various embodiments.

The following disclosure illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Overview

A set of embodiments provides methods, systems, and software that can be used, in many cases noninvasively, to quickly and accurately provide diagnostic information about a patient. In some cases, for example, these tools and techniques can be used to assess the effectiveness of hydration of a patient and/or the patient's hydration level. Such an assessment can include, without limitation, an estimate of the effectiveness at a current time, a prediction of the effectiveness at some point in the future, an estimate and/or prediction of a volume of fluid necessary for effective hydration, an estimate of the probability that a patient requires fluids, etc. In a particular set of embodiments, a device, which can be worn on the patient's body, can include one or more sensors that monitor a patient's physiological parameters. The device (or a computer in communication with the device) can analyze the data captured by the sensors and compare such data with a model (which can be generated in accordance with other embodiments) to assess the effectiveness of hydration, as described in further detail below.

Another diagnostic assessment that can be performed is an estimate of at what point a patient might suffer cardiovascular collapse. In fact, a number of different assessments, variously described in the Related Applications, can be performed in accordance with different embodiments. In an aspect of some embodiments, these assessments can be performed by calculating a patient's CRI multiple times before, during, and/or after a physical perturbation of the patient's body, and based on the variance of the calculated CRI values, assessing a physical state of the patient. Merely by way of example, in one embodiment, a patient's body might be perturbed by the patient performing a squat exercise (including, without limitation, a deep squat exercise), either as a body weight exercise or while bearing additional weight, and multiple values of a patient's CRI might be calculated based on physiological parameters (such as those described below and in the Related Applications) measured before, during, and/or after the squat exercise is performed. Based on the variance of the calculated CRI values, an estimate of the patient's hydration state can be calculated.

Another embodiment might employ a similar procedure, but using a different physical perturbation (including, without limitation, those described below and in the Related Applications). Further embodiments), and can make estimates or predictions about a number of physical states of the patient (including, without limitation, the estimations or predictions described in the Related Applications) based on calculations of CRI values based on physiological parameters measured before, during and/or after various types of physical perturbations.

Merely by way of example, one mode of physically perturbing a subject's body is to apply lower body negative pressure ("LBNP") to the body, using a LBNP chamber. Another mode of perturbation is to induce pressure changes (i.e., either positive pressure or negative pressure, or both) to the subject's airway or other body parts. One way to induce such pressure changes to the airway is through an impedance threshold device. An impedance threshold device ("ITD"), in general, can be any device that restricts inspiratory airflow, which can result in negative intrathoracic pressure, an increase in venous return to the heart, and/or an increase in stroke volume/blood flow/circulation. An intrathoracic pressure regulating device ("ITPR") can be considered a type of ITD, in that it functions in a similar way, on ventilated patients, by introducing an active vacuum source to the thorax through the respiratory circuit. The RESQGARD™ and RESQPOD™ devices, both available from Advanced Circulatory Systems, Inc., are examples of ITD devices that can be used to physically perturb a body, in accordance with certain embodiments.

Other devices, such as blood pressure cuffs and the like, can be used to induce positive pressure to desired areas of the body. Likewise, various techniques that might not require any additional equipment, can be used to perturb the body. For example, if the desired perturbation is to induce positive pressure on the subject's airway, a valsalva maneuver might be performed. Alternatively and/or additionally, positive pressure can be induced on an airway during spontaneous, unassisted breathing, or positive pressure can be induced on an airway during mechanical ventilation, e.g., through use of a ventilator.

Other types of physical perturbations are possible as well. Merely by way of example, in some cases, the delivery of medication and/or fluids (e.g., intravenously or otherwise) can serve as a physical perturbation. In other cases, the body may be perturbed through delivery of electrical current to the body of the subject (or a desired portion thereof, e.g., using an automatic implantable cardioverter defibrillator ("AICD"). More generally, a physical perturbation of the subject's body can be an action that imposes a physical change or stress on a subject's body (or a portion thereof) that results in a measurable change in a physiological parameter, such that the change can be used to enhance the medical monitoring process, or more particularly, facilitate the estimation and/or prediction of a physiological state of the subject.

Sometimes, the body will perturb itself such as when performing an exercise (e.g., a squat exercise, a sit-up exercise, etc.), a change in position (e.g., sitting or standing up), taking a spontaneous breath, or when there is a premature ventricular contraction (PVC) of the heart. Position changes can impact the cardiovascular system, leading to increasing or decreasing venous return and/or a rise or fall in blood pressure. A spontaneous breath leads to greater negative intrathoracic pressure, an increase in venous return, greater filling of the heart, augmentation of cardiac stroke volume and/or a change in blood pressure. PVCs cause compensatory pauses in the cardiac cycle, which lead to greater filling of the heart, augmentation of the stroke volume and/or a change in blood pressure. These various perturbations of the cardiopulmonary system can be monitored, and the body's response measured, to continuously estimate the physiological state and/or clinical condition of the patient.

As used herein, unless specifically indicated otherwise, physically perturbing any portion of a subject's body can be considered to be perturbing the patient's body itself. In some cases, physically perturbing the patient's body might involve the use of a perturbation device, although this is not necessary. The term "perturbation device," as used herein, means any device, whether operated manually or automatically, that can be used to produce a physical perturbation of the subject's body (or a portion thereof), in accordance with various embodiments. Examples include, but are not limited to, an LBNP chamber, ITD, blood pressure cuffs, and/or any other device that can exert a positive and/or negative pressure on a subject's body (or portion of a subject's body, such as the airway, extremities, etc.); or a fluid and/or medication delivery system, such as an auto-infuser, intravenous pump or auto-infuser, etc., an electricity delivery system, such as an automatic implantable cardioverter defibrillator or a pacemaker, a heating/cooling blanket, and/or any other type of physical stimulant (e.g., an induced change in the subject's position, an audible sound, a change in temperature or lighting, etc.).

Different embodiments can measure a number of different physiological parameters from the patient, and the analysis of those parameters can vary according to which parameters are measured (and which, according to the generated model, are found to be most predictive of the effectiveness of hydration, including the probability of the need for hydration and/or the volume of fluids needed). In some cases, the parameters themselves (e.g., continuous waveform data captured by a photoplethysmograph) can be analyzed against the model to make assessments of hydration effectiveness. In other cases, physiological parameters can be derived from the captured data, and these parameters can be used. Merely by way of example, as described further below and in the '483 application (already incorporated by reference), direct physiological data (captured by sensors) can be used to estimate a set of values of CRI, and this set of values of CRI can be used to assess the effectiveness of hydration. In yet other cases, the derived set of CRI values and raw sensor data can be used together to perform such an assessment.

For example, the '483 application describes a compensatory reserve monitor (also described as a cardiac reserve monitor or hemodynamic reserve monitor) that is able to estimate the compensatory reserve of a patient. In an aspect, this monitor quickly, accurately and/or in real-time can determine the probability of whether a patient is bleeding. In another aspect, the device can simultaneously monitor the patient's compensatory reserve by tracking the patient's CRI, to appropriately and effectively guide hydration and ongoing patient care. The same device (or a similar device) can also include advanced functionality to assess the effectiveness of hydration, based on the monitored CRI values, as explained in further detail below.

CRI is a hemodynamic parameter that is indicative of the individual-specific proportion of intravascular fluid reserve remaining before the onset of hemodynamic decompensation. CRI has values that range from 1 to 0, where values near 1 are associated with normovolemia (normal circulatory volume) and values near 0 are associated with the individual-specific circulatory volume at which hemodynamic decompensation occurs.

The mathematical formula of CRI, at some time "t" is given by the following equation:

$$CRI(t) = 1 - \frac{BLV(t)}{BLV_{HDD}} \quad \text{(Eq. 1)}$$

where BLV(t) is the intravascular volume loss ("BLV," also referred to as "blood loss volume" in the Related Applications) of a person at time "t," and $BLV_{HDD}$ is the intravascular volume loss of a person when they enter hemodynamic decompensation ("HDD"). Hemodynamic decompensation is generally defined as occurring when the systolic blood pressure falls below 70 mmHg. This level of intravascular volume loss is individual specific and will vary from subject to subject.

Lower body negative pressure ("LBNP") in some linear or nonlinear relationship $\lambda$ with intravascular volume loss:

$$BLV = \lambda \cdot LBNP \quad \text{(Eq. 2)}$$

can be used in order to estimate the CRI for an individual undergoing a LBNP experiment as follows:

$$CRI = 1 - \frac{BLV(t)}{BLV_{HDD}} \approx 1 - \frac{\lambda \cdot LBNP(t)}{\lambda \cdot LBNP_{HDD}} = 1 - \frac{LBNP(t)}{LBNP_{HDD}} \quad \text{(Eq. 3)}$$

where LBNP(t) is the LBNP level that the individual is experiencing at time "t," and, $LBNP_{HDD}$ is the LNPB level at which the individual will enter hemodynamic decompensation.

Using either CRI data, raw (or otherwise processed) sensor data, or both, various embodiments can assess the effectiveness of hydration. In one embodiment, the effectiveness of hydration ("HE") can be expressed as a value between 0 and 1; when HE=1, hydration is proceeding effectively, when HE=0, hydration is not producing the desired result, perhaps due to ongoing bleeding. (Of course, other embodiments can scale the value of HE differently). In an aspect of some embodiments, a general expression for the estimate of HE is as follows:

$$HE = f_{HE}(CRI_t, FV_t, S_t) \quad \text{(Eq. 4)}$$

where HE is a measure of hydration effectiveness, $f_{HE}(CRI_t, FV_t, S_t)$ is an algorithm embodied by a model generated empirically, e.g., using the techniques described with respect to FIG. 4 below, and/or in the Related Applications, $CRI_t$ is a time history of CRI values (which can range from a single set of CRI values to many hours of sets of CRI values), $FV_t$ is a time history of fluid volume being given to the patient (which can range from a single value to many hours of values), and $S_t$ is a time history of raw sensor values, such as physiological data measured by the sensors, as described elsewhere herein (which can range from one value to many hours of values).

The functional form of Eq. 4 is similar to, but not limited to, the form of the CRI model in the sense that time histories of $(CRI_t, FV_t, S_t)$ data gathered from human subjects at various levels of HE are compared to time histories of $(CRI_t, FV_t, S_t)$ for the current patient being monitored. The estimated HE for the current patient is then that which is the closest in $(CRI_t, FV_t, S_t)$ space to the previously gathered data.

While Eq. 4 is the general expression for HE, various embodiments might use subsets of the parameters considered in Eq. 4. For instance, in one embodiment, a model might consider only the volume of fluid and CRI data, without accounting for raw sensor input. In that case, HE can be calculated as follows:

$$HE = f_{HE}(CRI_t, FV_t). \quad \text{(Eq. 5)}$$

Similarly, some models might estimate HE based on sensor data, rather than first estimating CRI, in which case, HE can be expressed thusly:

$$HE = f_{HE}(FV_t, S_t). \quad \text{(Eq. 6)}$$

The choice of parameters to use in modeling HE is discretionary, and it can depend on what parameters are shown (e.g., using the techniques of FIG. 4, below) to result in the best prediction of HE.

In another aspect, the effectiveness of hydration can be assessed by estimating or predicting the volume, V, of fluid necessary for effective hydration of the patient. This volume, V, can indicate a volume of fluid needed for full hydration if therapy has not yet begun, and/or it can indicate a volume remaining for fully effective hydration if therapy is underway. Like HE, the value of V can be estimated/predicted using the modeling techniques described herein and in the Related Applications. In a general case, V can be expressed as the following:

$$V = f_v(CRI_t, FV_t, S_t) \quad \text{(Eq. 7)}$$

where V is an estimated volume of fluid needed by a patient to prevent over or under-hydration, $f_v(CRI_t, FV_t, S_t)$ is an algorithm embodied by a model generated empirically, e.g., using the techniques described with respect to FIG. 4 below, and/or in the Related Applications, $CRI_t$ is a time history of CRI values, $FV_t$ is a time history of fluid volume being given to the patient, and $S_t$ is a time history of physiological data received from the one or more sensors.

As with the estimate of HE, various embodiments can employ subsets of the parameters used in the general expression of Eq. 7. Thus, different embodiments might calculate V as follows:

$$V = f_v(CRI_t, FV_t) \quad \text{(Eq. 8)}$$

or $$V = f_v(FV_t, S_t). \quad \text{(Eq. 9)}$$

Yet another way of assessing effectiveness of hydration (which can even include assessing the need for hydration) is estimating the probability $P_f$ that the patient requires fluids; this probability can estimate the likelihood that the patient requires hydration if therapy has not been initiated, and/or, if hydration therapy is underway, the probability can estimate the likelihood that further hydration is necessary. The value of this probability, which can be expressed, e.g., as a percentage, as a decimal value between 0 and 1, etc. can be estimated using the following expression:

$$P_f = f_{P_f}(CRI_t, S_t) \quad \text{(Eq. 10)}$$

where $P_f$ is the estimated probability that the patient requires fluid, $f_{P_f}(CRI_t, S_t)$ is a relationship derived based on empirical study, $CRI_t$ is a time history of CRI values, and $S_t$ is a time history of physiological data received from the one or more sensors. Once again, this general expression can be employed, in various embodiments, using subsets of the parameters in the general expression, such as the following:

$$P_f = f_{P_f}(CRI_t) \quad \text{(Eq. 11)}$$

or $$P_f = f_{P_f}(S_t). \quad \text{(Eq. 12)}$$

Figure 2A:
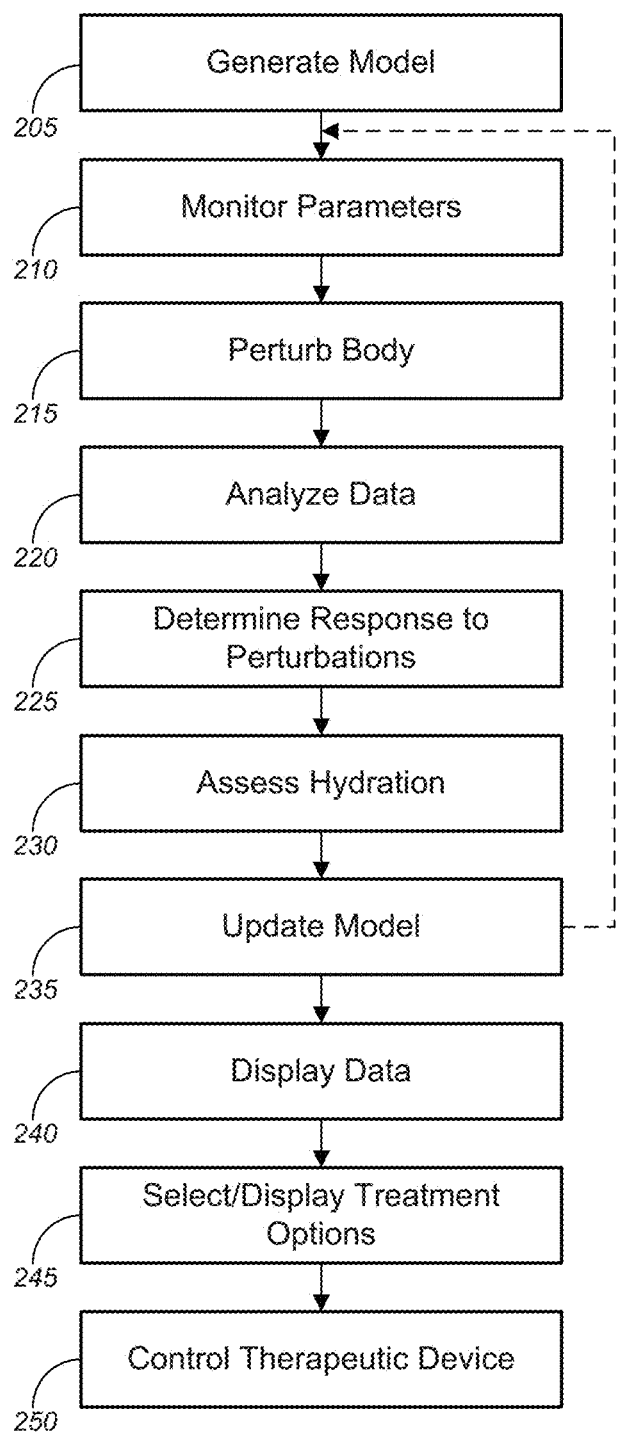
FIG. 2A is a process flow diagram illustrating a method of assessing effectiveness of hydration, in accordance with various embodiments.

In the estimate of any of HE, V, or $P_f$, the function $f$ expresses a relationship that is derived based on empirical study. In a set of embodiments, for example, various sensor data can be collected from test subjects before, during, and/or after hydration efforts, during hemorrhaging, or under other conditions that might simulate such situations. This sensor data can be analyzed to develop models, using techniques similar to those of FIG. 4 below, which can then be used to estimate various assessments of hydration effectiveness, using, e.g., the methods described below with respect to FIGS. 2 and 3.

A measure of CRI, HE, V, and/or $P_f$ can be useful in a variety of clinical settings, including but not limited to: 1) acute blood loss volume due to injury or surgery; 2) acute circulatory volume loss due to hemodialysis (also called intradialytic hypotension); and 3) acute circulatory volume loss due to various causes of dehydration (e.g. reduced fluid intake, vomiting, dehydration, etc.). A change in CRI can also herald other conditions, including, without limitation, changes in blood pressure, general fatigue, overheating, and certain types of illnesses, etc. Accordingly, the tools and techniques for estimating and/or predicting CRI can have a variety of applications in a clinical setting, including, without limitation, diagnosing such conditions.

Moreover, measures of CRI, HE, V, and/or $P_f$ can have applicability outside the clinical setting. For example, an athlete can be monitored (e.g., using a wrist-wearable hydration monitor) before, during, or after competition or training to ensure optimal performance (and overall health and recovery). In other situations, a person concerned about overall wellbeing can employ a similar hydration monitor to ensure that he or she is getting enough (but not too much) fluid, infants or adults can be monitored while ill to ensure that symptoms (e.g., vomiting, diarrhea, etc.) do not result in dehydration, and the like. Similarly, soldiers in the field (particularly in harsh conditions) can be monitored to ensure optimal operational readiness.

In various embodiments, a hydration monitor, a compensatory reserve monitor, a wrist-wearable sensor device, and/or another integrated system can include, but is not limited to, some or all of the following functionality, as described in further detail herein and in the Related Applications:

A. Estimating and/or displaying intravascular volume loss to hemodynamic decompensation (or cardiovascular collapse).

B. Estimating, predicting, and/or displaying a patient's compensatory reserve as an index that is proportional to an approximate measure of intravascular volume loss to CV collapse, recognizing that each patient has a unique reserve capacity.

C. Estimating, predicting, and/or displaying a patient's compensatory reserve as an index with a normative value at euvolemia (for example, CRI=1), representing a state in which the patient is normovolemic; a minimum value (for example, CRI=0) which implies no circulatory reserve and that the patient is experiencing CV collapse; and/or an excess value (for example, CRI>1) representing a state in which the patient is hypervolemic; the patient's normalized compensatory reserve can be displayed on a continuum between the minimum and maximum values (perhaps labeled by different symbols and/or colors depending on where the patient falls on the continuum).

D. Determining and/or displaying a probability that bleeding or intravascular volume loss has occurred.

E. Displaying an indicator that intravascular volume loss has occurred and/or is ongoing; as well as other measures of reserve, such as trend lines.

F. Estimating a patient's current blood pressure and/or predicting a patient's future blood pressure.

G. Estimating the current effectiveness of fluid resuscitation efforts.

H. Predicting the future effectiveness of fluid resuscitation efforts.

I. Estimating and/or predicting a volume of fluid necessary for effective resuscitation.

J. Estimating a probability that a patient needs fluids.

K. Estimating a hydration state of a patient or user.

L. Predicting a future hydration state of a patient or user.

M. Estimating and/or predicting a volume of fluid intake necessary for adequate hydration of a patient or user.

N. Estimating a probability that a patient is dehydrated.

In various embodiments, CRI, HE, V, and/or $P_f$ estimates can be (i) based on a fixed time history of patient monitoring (for example a 30 second or 30 heart beat window); (ii) based on a dynamic time history of patient monitoring (for example, monitoring for 200 minutes, the system may use all sensor information gathered during that time to refine and improve CRI estimates, hydration effectiveness assessments, etc.); (iii) based on either establishing baseline estimates when the patient is normovolemic (no volume loss has occurred); and/or (iv) based on NO baselines estimates when patient is normovolemic.

Certain embodiments can also recommend treatment options, based on the analysis of the patient's condition (including, without limitation, the estimated/predicted blood pressure, probability of bleeding, state of dehydration, and/or the patient's estimated and/or predicted CRI, and the like). Treatment options can include, without limitation, such things as optimizing hemodynamics, ventilator adjustments, IV fluid adjustments (e.g., controlling the flow rate of an IV pump or the drip rate of an IV drip), transfusion of blood or blood products, infusion of volume expanders, medication changes, changes in patient position and surgical therapy, and/or the like.

As one example, certain embodiments can be used to control an IV drip, IV pump, or rapid infuser, and/or the like, to infuse one or more of a crystalloid, colloid, or blood product into a patient. For instance, an embodiment might estimate the probability that a patient requires fluids and activate such a device in response to that estimate (or instruct a clinician to attach such a device to the patient and activate the device). The system might then monitor the progress of the hydration effort (through continual or periodic assessment of the effectiveness of hydration) and increase/decrease drip or flow rates accordingly.

As another example, certain embodiments can be used as an input for a hemodialysis procedure. For example, certain embodiments can predict how much intravascular (blood) volume can be safely removed from a patient during a hemodialysis process. For example, an embodiment might provide instructions to a human operator of a hemodialysis machine, based on estimates or predictions of the patient's CRI. Additionally and/or alternatively, such embodiments can be used to continuously self-adjust the ultra-filtration rate of the hemodialysis equipment, thereby completely avoiding intradialytic hypotension and its associated morbidity.

As yet another example, certain embodiments can be used to estimate and/or predict a dehydration state (and/or the amount of dehydration) in an individual (e.g., a trauma patient, an athlete, an elder living at home, etc.) and/or to provide treatment (either by providing recommendations to treating personnel or by directly controlling appropriate therapeutic equipment). For instance, if an analytical model indicates a relationship between CRI (and/or any other physiological phenomena that can be measured and/or estimated using the techniques described herein and in the Related Applications) and dehydration state, an embodiment can apply that model, using the techniques described herein, to estimate a dehydration state of the patient.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

In an aspect, a hydration monitor might comprise one or more sensors to obtain physiological data from a patient and a computer system in communication with the one or more sensors. The computer system might comprise one or more processors and a computer readable medium in communication with the one or more processors. The computer readable medium might have encoded thereon a set of instructions that, when executed by the one or more processors, causes the computer system to: receive a first set of physiological data from the one or more sensors at a first time in relation to a physical perturbation of the patient; calculate a first set of compensatory reserve index ("CRI") values of the patient; receive a second set of physiological data from the one or more sensors at a second time in relation to the physical perturbation of the patient; calculate a second set of CRI values of the patient; analyze the first and second sets of CRI values against a pre-existing CRI model; based at least in part on a relationship between the first and second sets of CRI values, estimate a hydration state of the patient; and display on a display device, an estimate of the hydration state of the patient.

According to some embodiments, the one or more sensors might comprise a finger cuff comprising a fingertip photoplethysmograph, and the computer system might comprise a wrist unit in communication with the fingertip photoplethysmograph, the wrist unit further comprising a wrist strap.

In some embodiments, estimating a hydration state of the patient might comprise determining whether the patient needs more fluids. In some cases, determining whether the patient needs more fluids might comprise determining whether the patient has an ongoing, progressive increase in fluid requirements (i.e., if the patient's hydration state is deteriorating), and/or the like. In some instances, determining whether the patient needs more fluids might comprise estimating how much fluid is needed, in some cases, based at least in part on how much fluid the patient has received between the first time and the second time in relation to the physical perturbation of the patient.

In another aspect, a method might comprise monitoring, with one or more sensors, physiological data of a patient and receiving a first set of physiological data from the one or more sensors at a first time in relation to a physical perturbation of the patient. The method might also comprise calculating a first set of compensatory reserve index ("CRI") values of the patient, receiving a second set of physiological data from the one or more sensors at a second time in relation to the physical perturbation of the patient, and calculating a second set of CRI values of the patient. The method might further comprise analyzing the first and second sets of CRI values against a pre-existing CRI model, based at least in part on a relationship between the first and second sets of CRI values, estimating a physiological state of the patient, and displaying on a display device, an estimate of the physiological state of the patient.

In some embodiments, the physical perturbation of the patient might comprise performance of an exercise, which might comprise a squat exercise, a sit-up exercise, and/or the like. According to some embodiments, the physical perturbation might comprise delivery of fluid to the patient. Alternatively, the physical perturbation might comprise introduction of positive or negative pressure to an airway of the patient. In some cases, the physiological state might be a hydration state of the patient. Alternatively, the physiological state might be an estimated point of cardiovascular collapse of the patient.

According to some embodiments, calculating the first or the second set of CRI values of the patient might comprise estimating a set of CRI values by comparing the physiological data to the pre-existing CRI model, which is constructed using the following formula: $CRI(t) = 1 - BLV(t)/BLV_{HDD}$, where $CRI(t)$ is the compensatory reserve index at time t, $BLV(t)$ is an intravascular volume loss of a test subject at time t, and $BLV_{HDD}$ is an intravascular volume loss at a point of hemodynamic decompensation of the test subject. In some instances, the physiological data might comprise waveform data, and estimating a set of CRI values of the patient might comprise comparing the waveform data with one or more sample waveforms generated by exposing each of one or more test subjects to a state of hemodynamic decompensation or near hemodynamic decompensation or to a series of states progressing towards hemodynamic decompensation, and monitoring physiological data of the test subjects. In some cases, the physiological data might comprise waveform data, and estimating a set of CRI values of the patient might comprise: comparing the waveform data with a plurality of sample waveforms, each of the sample waveforms corresponding to a different set of values of the compensatory reserve index to produce a similarity coefficient expressing a similarity between the waveform data and each of the sample waveforms; normalizing the similarity coefficients for each of the sample waveforms; and summing the normalized similarity coefficients to produce an estimated set of CRI values for the patient.

Merely by way of example, in some cases, at least one of the one or more sensors might comprise at least one of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, or an electronic stethoscope, and/or the like. In some instances, the physiological data might comprise blood pressure waveform data. Alternatively, the physiological data might comprise plethysmograph waveform data. In other cases, the physiological data might comprise photoplethysmograph ("PPG") waveform data.

According to some embodiments, the method might further comprise generating the pre-existing CRI model. In some instances, generating the pre-existing model might comprise: receiving data pertaining to one or more physiological parameters of a test subject to obtain a plurality of physiological data sets; directly measuring one or more physiological states of the test subject with a reference sensor to obtain a plurality of physiological state measurements; and correlating the received data with the physiological state measurements of the test subject. In some embodiments, the one or more physiological states might comprise one or more states comprising at least one of reduced circulatory system volume, blood loss, added fluids to blood volume, dehydration, hydration state, cardiovascular collapse, near-cardiovascular collapse, euvolemia, or hypervolemia, and/or the like. In some cases, correlating the received data with the physiological state measurements of the test subject might comprise: identifying a most predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter, and wherein each of the one or more outcomes $o_k$ represents a physiological state measurement; autonomously learning a set of probabilistic predictive models $\hat{o}_k = M_K(S_K)$, where $\hat{o}_k$ is a prediction of outcome $\hat{o}_k$ derived from a model $M_k$ that uses as inputs values obtained from the most predictive set of signals $S_k$; and repeating the operation of autonomously learning incrementally from data that contains examples of values of signals $s_1, s_2, \ldots, s_D$ and corresponding outcomes $o_1, o_2, \ldots, o_K$.

In some embodiments, estimating a physiological state of the patient might comprise a hydration state of the patient and determining whether the patient needs more fluids. In some cases, determining whether the patient needs more fluids might comprise determining whether the patient has an ongoing, progressive increase in fluid requirements (i.e., if the patient's hydration state is deteriorating), and/or the like. In some instances, determining whether the patient needs more fluids might comprise estimating how much fluid is needed, in some cases, based at least in part on how much fluid the patient has received between the first time and the second time in relation to the physical perturbation of the patient.

In yet another aspect, an apparatus might comprise a non-transitory computer readable medium having encoded thereon a set of instructions executable by one or more computers to: receive a first set of physiological data from one or more sensors at a first time in relation to a physical perturbation of a patient, the one or more sensors monitoring physiological data of the patient; calculate a first set of compensatory reserve index ("CRI") values of the patient; receive a second set of physiological data from the one or more sensors at a second time in relation to the physical perturbation of the patient; calculate a second set of CRI values of the patient; analyze the first and second sets of CRI values against a pre-existing CRI model; based at least in part on a relationship between the first and second sets of CRI values, estimate a physiological state of the patient; and display on a display device, an estimate of the physiological state of the patient.

In still another aspect, a system might comprise a processor and a non-transitory computer readable medium having encoded thereon a set of instructions that, when executed by the processor, causes the system to: receive a first set of physiological data from one or more sensors at a first time in relation to a physical perturbation of a patient, the one or more sensors monitoring physiological data of the patient; calculate a first set of compensatory reserve index ("CRI") values of the patient; receive a second set of physiological data from the one or more sensors at a second time in relation to the physical perturbation of the patient; calculate a second set of CRI values of the patient; analyze the first and second sets of CRI values against a pre-existing CRI model; based at least in part on a relationship between the first and second sets of CRI values, estimate a physiological state of the patient; and display on a display device, an estimate of the physiological state of the patient.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Exemplary Systems and Methods

FIG. 1A provides a general overview of a system provided by certain embodiments. The system includes a computer system 100 in communication with one or more sensors 105, which are configured to obtain physiological data from the subject (e.g., animal or human test subject or patient) 110. In one embodiment, the computer system 100 comprises a Lenovo THINKPAD X200, 4 GB of RAM with Microsoft WINDOWS 7 operating system and is programmed with software to execute the computational methods outlined herein. The computational methods can be implemented in MATLAB 2009b and C++ programming languages. A more general example of a computer system 100 that can be used in some embodiments is described in further detail below. Even more generally, however, the computer system 100 can be any system of one or more computers that are capable of performing the techniques described herein. In a particular embodiment, for example, the computer system 100 is capable of reading values from the physiological sensors 105, generating models of physiological state from those sensors, and/or employing such models to make individual-specific estimations, predictions, or other diagnoses, displaying the results, recommending and/or implementing a therapeutic treatment as a result of the analysis, and/or archiving (or learning) these results for use in future, e.g., model building and making predictions, etc.

The sensors 105 can be any of a variety of sensors (including without limitation those described herein) for obtaining physiological data from the subject. An exemplary sensor suite might include a Finometer sensor for obtaining a noninvasive continuous blood pressure waveform, a pulse oximeter sensor, an Analog to Digital Board (National Instruments USB-9215A 16-Bit, 4 channel) for connecting the sensors (either the pulse oximeter and/or the finometer) to the computer system 100. More generally, in an embodiment, one or more sensors 105 might obtain, e.g., using one or more of the techniques described herein, continuous physiological waveform data, such as continuous blood pressure or the like. Input from the sensors 105 can constitute continuous data signals and/or outcomes that can be used to generate, and/or can be applied to, a predictive model as described below.

In some cases, the structure might include a therapeutic device 115 (also referred to herein as a "physiological assistive device"), which can be controlled by the computer system 100 to administer therapeutic treatment, in accordance with the recommendations developed by analysis of a patient's physiological data. In a particular embodiment, the therapeutic device might comprise hemodialysis equipment (also referred to as a hemodialysis machine), which can be controlled by the computer system 100 based on the estimated CRI of the patient, as described in further detail below. Further examples of therapeutic devices in other embodiments can include, without limitation, a cardiac assist device, a ventilator, an automatic implantable cardioverter defibrillator ("AICD"), pacemakers, an extracorporeal membrane oxygenation circuit, a positive airway pressure ("PAP") device (including without limitation a continuous positive airway pressure ("cPAP") device or the like), an anesthesia machine, an integrated critical care system, a medical robot, intravenous and/or intra-arterial pumps that can provide fluids and/or therapeutic compounds (e.g., through intravenous injection), intravenous drips, a rapid infuser, a heating/cooling blanket, and/or the like.

Figure 1B:
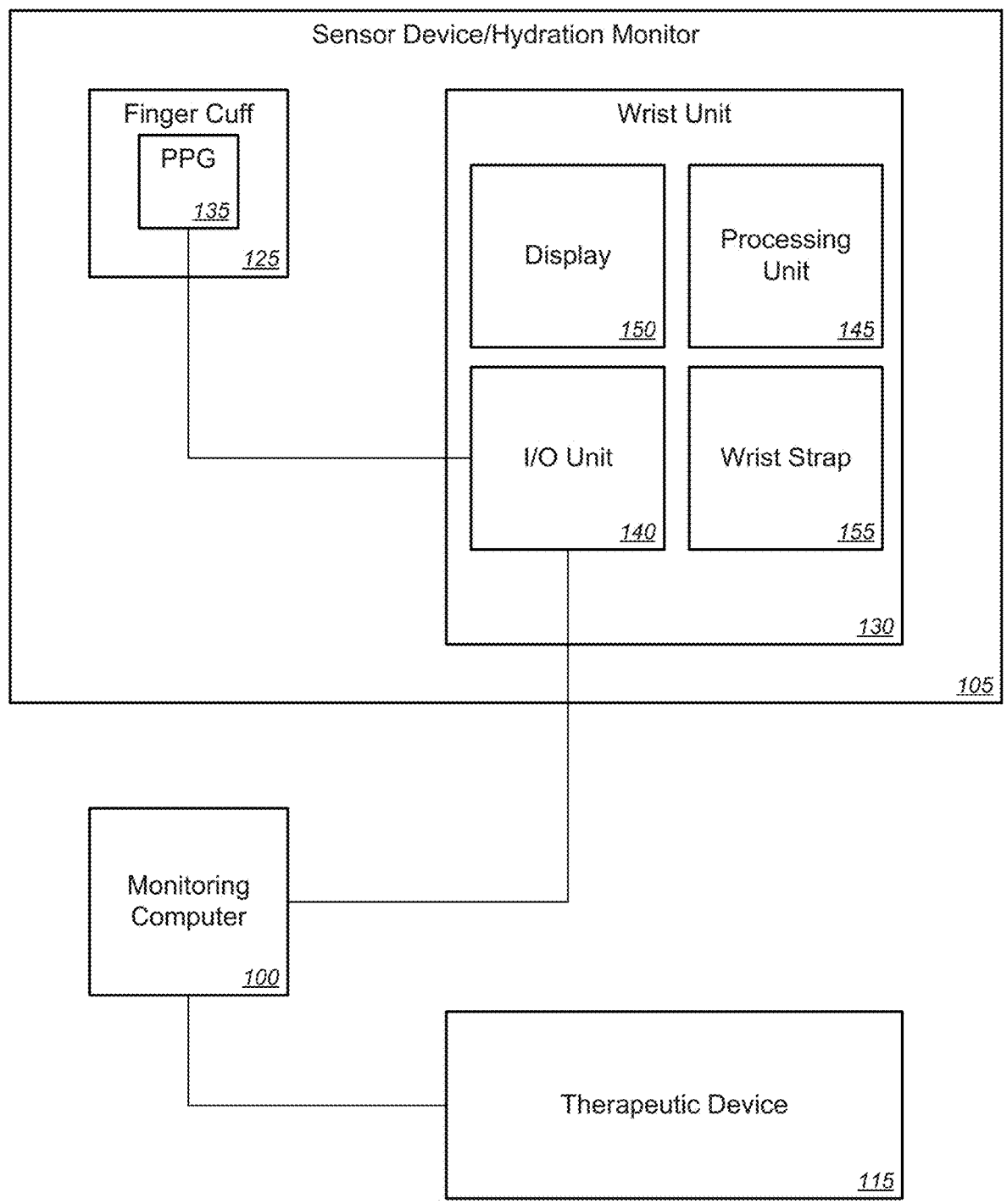
FIG. 1B is a schematic diagram illustrating a sensor system that can be worn on a patient's body, in accordance with various embodiments.

FIG. 1B illustrates in more detail an exemplary sensor device 105, which can be used in the system 100 described above. (It should be noted, of course, that the depicted sensor device 105 of FIG. 1B is not intended to be limiting, and different embodiments can employ any sensor that captures suitable data, including without limitation sensors described elsewhere in this disclosure and in the Related Applications.) The illustrated sensor device 105 is designed to be worn on a patient's wrist and therefore can be used both in clinical settings and in the field (e.g., on any person for whom monitoring might be beneficial, for a variety of reasons, including without limitation assessment of blood pressure and/or hydration during athletic competition or training, daily activities, military training or action, etc.). In one aspect, the sensor device 105 can serve as an integrated hydration monitor, which can assess hydration as described herein, display an indication of the assessment, recommend therapeutic action based on the assessment, or the like, in a form factor that can be worn during athletic events and/or daily activities.

Hence, the exemplary sensor 105 device (hydration monitor) includes a finger cuff 125 and a wrist unit 130. The finger cuff 125 includes a fingertip sensor 135 (in this case, a PPG sensor) that captures data based on physiological conditions of the patient, such as PPG waveform data. The sensor 135 communicates with an input/output unit 140 of the wrist unit 130 to provide output from the sensor 135 to a processing unit 145 of the wrist unit 130. Such communication can be wired (e.g., via a standard—such as USB—or proprietary connector on the wrist unit 130) and/or wireless (e.g., via Bluetooth, such as Bluetooth Low Energy ("BTLE"), near field connection ("NFC"), WiFi, or any other suitable radio technology).

In different embodiments, the processing unit can have different types of functionality. For example, in some cases, the processing unit might simply act to store and/or organize data prior to transmitting the data through the I/O unit 140 to a monitoring computer 100, which might perform data analysis, control a therapeutic device 115, etc. In other cases, however, the processing unit 145 might act as a specialized computer (e.g., with some or all of the components described in connection with FIG. 5, below and/or some or all of the functionality ascribed to the computer 100 of FIGS. 1A and 1B), such that the processing unit can perform data analysis onboard, e.g., to estimate and/or predict a patient's current and/or future blood pressure. As such, the wrist unit 105 might include a display, which can display any output described herein, including, without limitation, estimated and/or predicted values (e.g., of CRI, blood pressure, hydration status, etc.), data captured by the sensor (e.g., heart rate, pulse ox, etc.), and/or the like.

In some cases, the wrist unit 130 might include a wrist strap 155 that allows the unit to be worn on the wrist, similar to a wrist watch or a wrist-mounted fitness tracker. Of course, other options are available to facilitate transportation of the sensor device 105 with a patent. More generally, the sensor device 105 might not include all of the components described above, and/or various components might be combined and/or reorganized; once again, the embodiment illustrated by FIG. 1B should be considered to be only illustrative, and not limiting, in nature.

FIGS. 2A, 2B, 3A, 3B, and 4 illustrate methods in accordance with various embodiments. While the methods of FIGS. 2A, 2B, 3A, 3B, and 4 are illustrated, for ease of description, as different methods, it should be appreciated that the various techniques and procedures of these methods can be combined in any suitable fashion, and that, in some embodiments, the methods depicted by FIGS. 2A, 2B, 3A, 3B, and 4 can be considered interoperable and/or as portions of a single method. Similarly, while the techniques and procedures are depicted and/or described in a certain order for purposes of illustration, it should be appreciated that certain procedures may be reordered and/or omitted within the scope of various embodiments. Moreover, while the methods illustrated by FIGS. 2A, 2B, 3A, 3B, and 4 can be implemented by (and, in some cases, are described below with respect to) the computer system 100 of FIG. 1 (or other components of the system, such as the sensor 105 of FIGS. 1A and 1B), these methods may also be implemented using any suitable hardware implementation. Similarly, while the computer system 100 of FIG. 1 (and/or other components of such a system) can operate according to the methods illustrated by FIGS. 2A, 2B, 3A, 3B, and 4 (e.g., by executing instructions embodied on a computer readable medium), the system 100 can also operate according to other modes of operation and/or perform other suitable procedures.

Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

By way of non-limiting example, various embodiments can comprise a method for using sensor data to assess the effectiveness of fluid resuscitation of a patient and/or the hydration of a patient. FIG. 2 illustrates an exemplary method 200 in accordance with various embodiments. The method 200 might comprise generating a model, e.g., with a computer system, against which patient data can be analyzed to estimate and/or predict various physiological states (block 205). In a general sense, generating the model can comprise receiving data pertaining to a plurality of more physiological parameters of a test subject to obtain a plurality of physiological data sets. Such data can include PPG waveform data to name one example, and/or any other type of sensor data including, without limitation, data captured by other sensors described herein and in the Related Applications.

Generating a model can further comprise directly measuring one or more physiological states of the test subject with a reference sensor to obtain a plurality of physiological state measurements. The one or more physiological states can include, without limitation, states of various volumes of blood loss and/or fluid resuscitation, and/or various states of hydration and/or dehydration. (In other embodiments, different states can include a state of hypervolemia, a state of euvolemia, and/or a state of cardiovascular collapse (or near-cardiovascular collapse), and/or can include states that have been simulated, e.g., through use of an LBNP apparatus or the like.) Other physiological states that can be used to generate a model are described elsewhere herein and in the Related Applications.

Generating the model can further comprise correlating the physiological state(s) with the measured physiological parameters. There are a variety of techniques for generating a model in accordance with different embodiments, using these general functions. One exemplary technique for generating a model of a generic physiological state is described below with respect to FIG. 4, below, which provides a technique using a machine-learning algorithm to optimize the correlation between measured physiological parameters (such as PPG waveform data, to name one example) and physical states (e.g., various blood volume states, including states where a known volume of blood loss has occurred and/or a known volume of fluid resuscitation has been administered, various states of hydration and/or dehydration, etc.). It should be appreciated, however, that any suitable technique or model may be employed in accordance with various embodiments.

A number of physiological states can be modeled, and a number of different conditions can be imposed on test subjects as part of the model generation. For example, physiological states that can be induced (or monitored when naturally occurring) in test subjects include, without limitation, reduced circulatory system volume, known volume of blood loss, specified amounts of fluids added to blood volume, dehydration, cardiovascular collapse or near-cardiovascular collapse, euvolemia, hypervolemia, low blood pressure, high blood pressure, normal blood pressure, and/or the like.

Merely by way of example, in one set of embodiments, a number of physiological parameters of a plurality of test subjects might be measured. In some cases, a subject might undergo varying, measured levels of blood loss (either real or simulated) or intravenous fluid addition. Using the method described below with respect to FIG. 4 (or other, similar techniques, many of which are described in the Related Applications), the system can determine which sensor information most effectively differentiates between subjects at different blood loss/addition volume levels.

Additionally and/or alternatively to using direct (e.g., raw) sensor data to build such models, some embodiments might construct a model based on data that is derived from sensor data. Merely by way of example, one such model might use, as input values, CRI values of test subjects in different blood loss and/or volume addition conditions. Accordingly, the process of generating a model might first comprise building a model of CRI, and then, from that model, building a model of hydration effectiveness. (In other cases, a hybrid model might consider both raw sensor data and CRI data.)

A CRI model can be generated in different ways. For example, in some cases, one or more test subjects might be subjected to LBNP. In an exemplary case, LBNP data is collected from human subjects being exposed to progressively lower levels of LBNP, until each subject experiences hemodynamic decompensation, at which time LBNP is released and the subject recovers. Each level of LBNP represents an additional amount of blood loss. During these tests, physiological data (including, without limitation, waveform data, such as continuous non-invasive blood pressure data, etc.) can be collected before, during, and/or after the application of the LBNP. As noted above, a relationship (as expressed by Equation 2) can be identified between LBNP and intravascular volume loss, and this relationship can be used to estimate CRI. Hence, LBNP studies form a framework (methodology) for the development of the hemodynamic parameter referred to herein as CRI and can be used to generate models of this parameter.

More generally, several different techniques that induce a physiological state of reduced volume in the circulatory system, e.g., to a point of cardiovascular collapse (i.e., hemodynamic decompensation) or to a point near cardiovascular collapse, can be used to generate such a model. LBNP can be used to induce this condition, as noted above. In some cases, such as in a study described below, dehydration can be used to induce this condition as well. Other techniques are possible as well. Similarly, data collected from a subject in a state of euvolemia, dehydration, hypervolemia, and/or other states might be used to generate a CRI model in different embodiments.

At block 210, the method 200 comprises monitoring, with one or more sensors, physiological data of a patient. As noted above, a variety of physical parameters can be monitored, invasively and/or non-invasively, depending on the nature of the anticipated physiological state of the patient. In an aspect, monitoring the one or more physical parameters might comprise receiving, e.g., from a physiological sensor, continuous waveform data, which can be sampled as necessary. Such data can include, without limitation, plethysmograph waveform data, PPG waveform data (such as that generated by a pulse oximeter), and/or the like.

At block 215, the method comprises perturbing the patient's body, or a portion thereof. (As used herein, unless specifically indicated otherwise, physically perturbing any portion of a subject's body can be considered to be perturbing the patient's body itself.) In some cases, physically perturbing the patient's body might involve the use of a perturbation device, as described above, although this is not necessary. In some cases, the body might perturb itself through a change in position, a spontaneous breath, or a premature ventricular contraction or other cardiac dysrhythmia, to name a few examples. In such cases, perturbing the patient's body might simply comprise monitoring and/or detecting the self-perturbation of the body. Many different types of physical perturbations are described above, and any of these, or other modes of perturbation may be employed in accordance with the method 200.

The method 200 might further comprise analyzing, with a computer system (e.g., a monitoring computer 100 and/or a processing unit 135 of a sensor unit, as described above), the physiological data (block 220). In some cases, the physiological data is analyzed against a pre-existing model (which might be generated as described above and which in turn, can be updated based on the analysis, as described in further detail below and in the Related Applications).

Merely by way of example, in some cases, sensor data can be analyzed directly against a generated model to assess the effectiveness of hydration (which can include estimating current values, and/or predicting future values for any or all of HE, V, and/or $P_f$, as expressed above. For example, the sensor data can be compared to determine similarities with models that estimate and/or predict any of these values. Merely by way of example, an input waveform captured by a sensor from a patient might be compared with sample waveforms generated by models for each of these values.

In a particular aspect, the sensor data is analyzed to determine a patient response to the one or more physical perturbations (block 225). This analysis might, comprise, for example, identifying a change in a patient's CRI values (which can be calculated, e.g., using the technique described with respect to the method 300, discussed below with regard to FIG. 3A), based on data samples taken before the perturbation, at one or more points during the perturbation, and/or after the perturbation. In an aspect, the analysis might comprise analyzing the input data against a model of a specified physiological state. In some cases, the model is pre-existing (i.e., generated prior to receiving the input data), although, as noted above, the model can be refined using the input data and the results of the analysis itself. In an exemplary case, the model provides an algorithm to which the input data can be applied, to produce output data relating to an estimated/predicted physiological state of the patient that corresponds to the patient's measured physiological parameters.

Figure 2B:
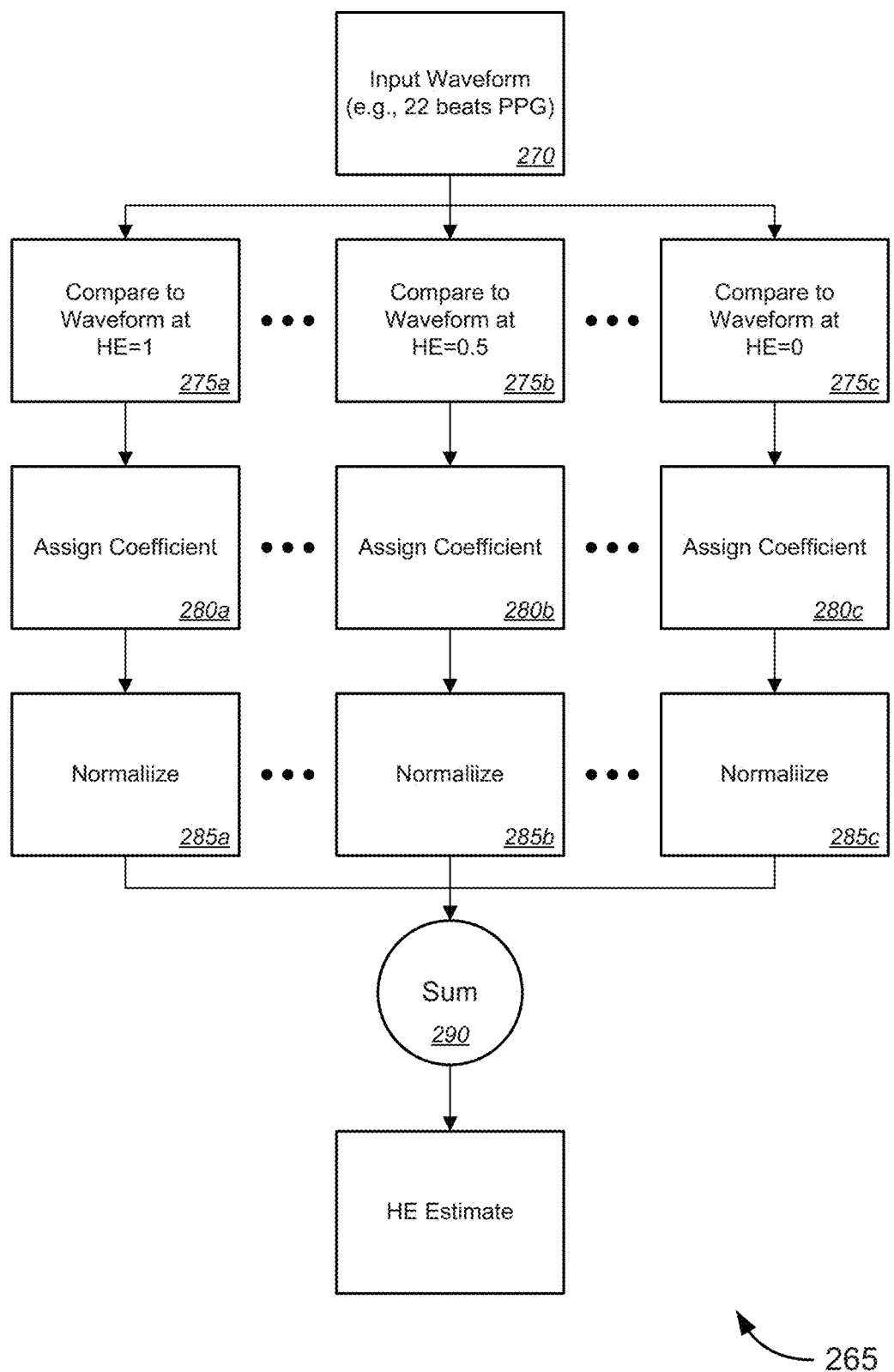
FIG. 2B illustrates a technique for assessing effectiveness of hydration, in accordance with various embodiments.

For example, the technique 265 (as shown in FIG. 2B) provides one method for deriving an estimate of HE in accordance with some embodiments. It should be noted that the technique 265 is presented as an example only, and that while this technique 265 estimates HE from raw sensor data, similar techniques can be used to estimate or predict HE, V, and/or $P_f$ from raw sensor data, from CRI data, and/or from a combination of both. For example, one model might produce a first estimate of HE from raw sensor data, produce a second estimate of HE from estimated CRI values, and then combine those estimates (in either weighted or unweighted fashion) to produce a hybrid HE estimate. Moreover, this technique 265 can be used to estimate HE (or any other physical state disclosed in the Related Applications) from variations in CRI data (which variations themselves can be used as input data to the technique 265).

The illustrated technique 265 comprises sampling waveform data (e.g., any of the data described herein and in the Related Applications, including without limitation arterial waveform data, such as continuous PPG waveforms and/or continuous noninvasive blood pressure waveforms) for a specified period, such as 22 or 32 heartbeats (block 270). Alternatively and/or additionally, multiple CRI data points can be used as the data sample. That sample is compared with a plurality of waveforms (or data points) of reference data corresponding to HE values (block 275), which in this case range from 0 to 1 using the scale described above (but alternatively might use any appropriate scale). These reference waveforms are derived as part of the model developed using the algorithms described in this and the Related Applications, might be the result of experimental data, and/or the like. In effect, these reference waveforms reflect the relationship $f$ from Eq. 6, above.

According to the technique 265, the sample might be compared with waveforms corresponding to a HE=1 (block 275a), HE=0.5 (block 275b), and HE=0 (block 275c), as illustrated. (As illustrated by the ellipses on FIG. 2B, any number of sample waveforms can be used for the comparison; for example, if there is a nonlinear relationship between the measured sensor data and the HE values, more sample waveforms might provide for a better comparison.) From the comparison, a similarity coefficient is calculated (e.g., using a least squares or similar analysis) to express the similarity between the sampled waveform and each of the reference waveforms (block 280). These similarity coefficients can be normalized (if appropriate) (block 285), and the normalized coefficients can be summed (block 390) to produce an estimated HE value of the patient.

In other cases, similar techniques can be used to analyze data against a model based on parameters derived from direct sensor measurements. (In one aspect, such operations can be iterative in nature, by generating the derived parameters—such as CRI, to name one example—by analyzing the sensor data against a first model, and then analyzing the derived parameters, and in particular cases, variance in derived parameters, such as CRI, against a second model.)

Figure 3A:
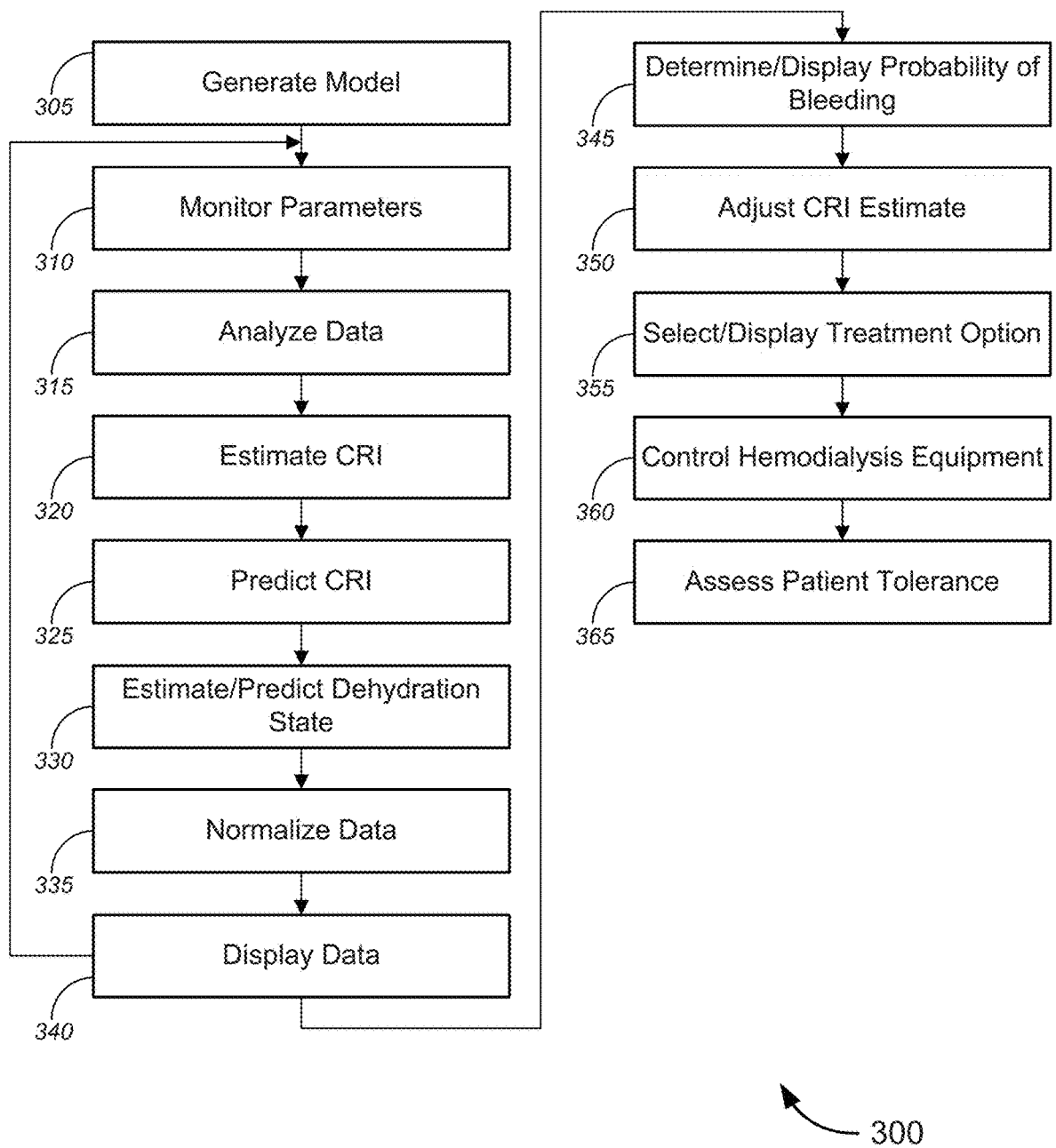
FIG. 3A is a process flow diagram illustrating a method estimating a patient's compensatory reserve and/or dehydration state, in accordance with various embodiments.

For example, FIG. 3A illustrates a method 300 of calculating a patient's CRI, which can be used (in some embodiments) as a parameter that can be analyzed to assess the effectiveness of hydration (including the probability that fluids are needed and/or the estimated volume of fluid necessary for effective hydration). The method 300 includes generating a model of CRI (block 305), monitoring physiological parameters (310) and analyzing the monitored physical parameters (block 315), using techniques such as those described above and in the Related Applications, for example.

Based on this analysis, the method 300, in an exemplary embodiment, includes estimating, with the computer system, a compensatory reserve (or CRI) of the patient, based on analysis of the physiological data (block 320). In some cases, the method might further comprise predicting, with the computer system, the compensatory reserve (or CRI) of the patient at one or more time points in the future, based on analysis of the physiological data (block 325). The operations to predict a future value of a parameter can be similar to those for estimating a current value; in the prediction context, however, the applied model might correlate measured data in a test subject with subsequent values of the diagnostic parameter, rather than contemporaneous values. It is worth noting, of course, that in some embodiments, the same model can be used to both estimate a current value and predict future values of a physiological parameter.

The estimated and/or predicted compensatory reserve of the patient can be based on several factors. Merely by way of example, in some cases, the estimated/predicted compensatory reserve (or CRI) can be based on a fixed time history of monitoring the physiological data of the patient and/or a dynamic time history of monitoring the physiological data of the patient. In other cases, the estimated/predicted compensatory reserve can be based on a baseline estimate of the patient's compensatory reserve established when the patient is euvolemic. In still other cases, the estimate and/or prediction might not be based on a baseline estimate of the patient's compensatory reserve established when the patient is euvolemic.

Figure 3B:
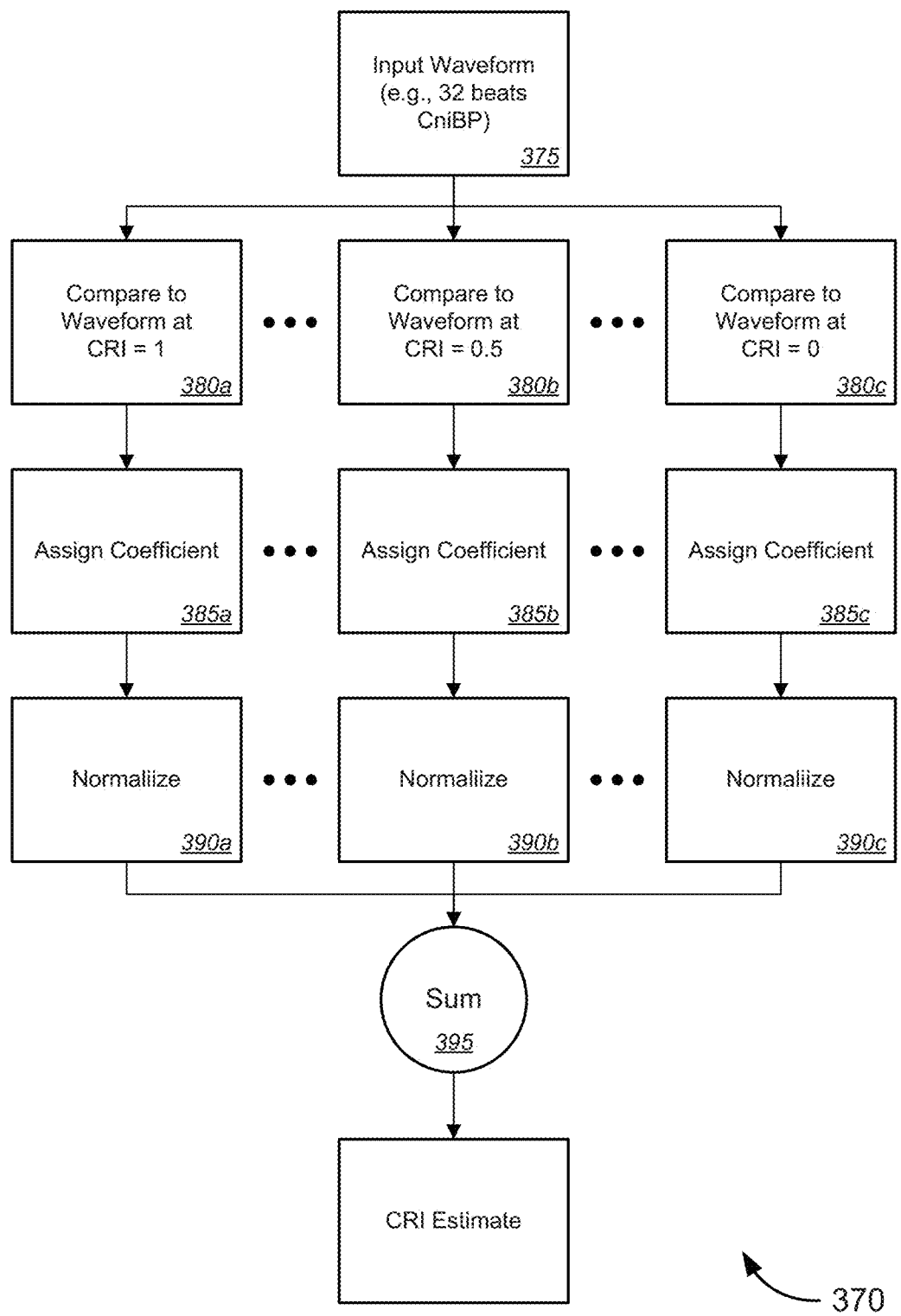
FIG. 3B illustrates a technique for estimating and/or predicting a patient's compensatory reserve index, in accordance with various embodiments.

Merely by way of example, FIG. 3B illustrates one technique 370 for deriving an estimate of CRI in accordance with some embodiments similar to the technique 265 described above with respect to FIG. 2B for deriving an assessment of hydration effectiveness directly from sensor data (and, in fact, CRI can be derived as described herein, and that derived set of values can be used, alone or with raw sensor data, to assess such effectiveness). The illustrated technique comprises sampling waveform data (e.g., any of the data described herein and in the Related Applications, including without limitation arterial waveform data, such as continuous PPG waveforms and/or continuous noninvasive blood pressure waveforms) for a specified period, such as 32 heartbeats (block 375). That sample is compared with a plurality of waveforms of reference data corresponding to different sets of CRI values (block 380). (These reference waveforms might be derived using the algorithms described in the Related applications, might be the result of experimental data, and/or the like). Merely by way of example, the sample might be compared with waveforms corresponding to a CRI of 1 (block 380a), a CRI of 0.5 (block 380b), and a CRI of 0 (block 380c), as illustrated. From the comparison, a similarity coefficient is calculated (e.g., using a least squares or similar analysis) to express the similarity between the sampled waveform and each of the reference waveforms (block 385). These similarity coefficients can be normalized (if appropriate) (block 390), and the normalized coefficients can be summed (block 395) to produce an estimated value or set of values of the patient's CRI.

Returning to FIG. 3A, the method 300 can comprise estimating and/or predicting a patient's dehydration state (block 330). The patient's state of dehydration can be expressed in a number of ways. For instance, the state of dehydration might be expressed as a normalized value (for example, with 1.0 corresponding to a fully hydrated state and 0.0 corresponding to a state of morbid dehydration). In other cases, the state of dehydration might be expressed as a missing volume of fluid or as a volume of fluid present in the patient's system, or using any other appropriate metric.

A number of techniques can be used to model dehydration state. Merely by way of example, as noted above (and described in further detail below), the relationship between a patient's compensatory reserve and level of dehydration can be modeled. Accordingly, in some embodiments, estimating a dehydration state of the patient might comprise estimating the compensatory reserve (e.g., CRI) of the patient, and then, based on that estimate and the known relationship, estimating the dehydration state. Similarly, a predicted value of compensatory reserve (or CRI) at some point in the future can be used to derive a predicted dehydration state at that point in the future. Other techniques might use a parameter other than CRI to model dehydration state.

The method 300 might further comprise normalizing the results of the analysis (block 335), such as the compensatory reserve, dehydration state, and/or probability of bleeding, to name a few examples. Merely by way of example, the estimated/predicted compensatory reserve of the patient can be normalized relative to a normative normal blood volume value corresponding to euvolemia, a normative excess blood volume value corresponding to circulatory overload, and a normative minimum blood volume value corresponding to cardiovascular collapse. Any values can be selected as the normative values. Merely by way of example, in some embodiments, the normative excess blood volume value is >1, the normative normal blood volume value is 1, and the normative minimum blood volume value is 0. As an alternative, in other embodiments, the normative excess blood volume value might be defined as 1, the normative normal blood volume value might be defined as 0, and the normative minimum blood volume value at the point of cardiovascular collapse might be defined as −1. As can be seen from these examples, different embodiments might use a number of different scales to normalize CRI and other estimated parameters.

In an aspect, normalizing the data can provide benefits in a clinical setting, because it can allow the clinician to quickly make a qualitative judgment of the patient's condition, while interpretation of the raw estimates/predictions might require additional analysis. Merely by way of example, with regard to the estimate of the compensatory reserve (or CRI) of the patient, that estimate might be normalized relative to a normative normal blood volume value corresponding to euvolemia and a normative minimum blood volume value corresponding to cardiovascular collapse. Once again, any values can be selected as the normative values. For example, if the normative normal blood volume is defined as 1, and the normative minimum blood volume value is defined as 0, the normalized value, falling between 0.0 and 1.0 can quickly apprise a clinician of the patient's location on a continuum between euvolemia and cardiovascular collapse. Similar normalizing procedures can be implemented for other estimated data (such as probability of bleeding, dehydration, and/or the like).

The method 300 might further comprise displaying data with a display device (block 340). Such data might include an estimate and/or prediction of the compensatory reserve (or CRI) of the patient and/or an estimate and/or prediction of the patient's dehydration state. A variety of techniques can be used to display such data. Merely by way of example, in some cases, displaying the estimate of the compensatory reserve (or CRI) of the patient might comprise displaying the normalized estimate of the compensatory reserve (or CRI) of the patient. Alternatively and/or additionally, displaying the normalized estimate of the compensatory reserve of the patient might comprise displaying a graphical plot showing the normalized excess blood volume value, the normalized normal blood volume value, the normalized minimum blood volume value, and the normalized estimate of the compensatory reserve (e.g., relative to the normalized excess blood volume value, the normalized normal blood volume value, the normalized minimum blood volume value).

In some cases, the method 300 might comprise repeating the operations of monitoring physiological data of the patient, analyzing the physiological data, and estimating (and/or predicting) the compensatory reserve of the patient, to produce a new estimated (and/or predicted) compensatory reserve of the patient. Thus, displaying the estimate (and/or prediction) of the compensatory reserve of the patient might comprises updating a display of the estimate of the compensatory reserve to show the new estimate (and/or prediction) of the compensatory reserve, in order to display a plot of the estimated compensatory reserve over time. Hence, the patient's compensatory reserve can be repeatedly estimated and/or predicted on any desired interval (e.g., after every heartbeat), on demand, etc.

In further embodiments, the method 300 can further comprise determining a probability that the patient is bleeding, and/or displaying, with the display device, an indication of the probability that the patient is bleeding (block 345). For example, some embodiments might generate a model based on data that removes fluid from the circulatory system (such as LBNP, dehydration, etc.). Another embodiment might generate a model based on fluid removed from a subject voluntarily, e.g., during a blood donation, based on the known volume (e.g., 500 cc) of the donation. Based on this model, using techniques similar to those described above, a patient's physiological data can be monitored and analyzed to estimate a probability that the patient is bleeding (e.g., internally).

In some cases, the probability that the patient is bleeding can be used to adjust the patient's estimated CRI (block 350). Specifically, give a probability of bleeding expressed as Pr_Bleed at a time t, the adjusted value of CRI can be expressed as:

$$CRI_{Adjusted}(t)=1-((1-CRI(t) \times Pr\_Bleed(t)). \quad \text{(Eq. 13)}$$

Given this relationship, the estimated CRI can be adjusted to produce a more accurate diagnosis of the patient's condition at a given point in time.

The method 300 might comprise selecting, with the computer system, a recommended treatment option for the patient, and/or displaying, with the display device, the recommended treatment option (block 355). The recommended treatment option can be any of a number of treatment options, including, without limitation, optimizing hemodynamics of the patient, a ventilator adjustment, an intravenous fluid adjustment, transfusion of blood or blood products to the patient, infusion of volume expanders to the patient, a change in medication administered to the patient, a change in patient position, and surgical therapy.

In a specific example, the method 300 might comprise controlling operation of hemodialysis equipment (block 360), based at least in part on the estimate of the patient's compensatory reserve. Merely by way of example, a computer system that performs the monitoring and estimating functions might also be configured to adjust an ultra-filtration rate of the hemodialysis equipment in response to the estimated CRI values of the patient. In other embodiments, the computer system might provide instructions or suggestions to a human operator of the hemodialysis equipment, such as instructions to manually adjust an ultra-filtration rate, etc.

In some embodiments, the method 300 might include assessing the tolerance of an individual to blood loss, general volume loss, and/or dehydration (block 365). For example, such embodiments might include estimating a patient's CRI based on the change in a patient's position (e.g., from lying prone to standing, lying prone to sitting, and/or sitting to standing). Based on changes to the patient's CRI in response to these maneuvers, the patient's sensitivity to blood loss, volume loss, and/or dehydration can be measured. In an aspect, this measurement can be performed using a CRI model generated as described above; the patient can be monitored using one or more of the sensors described above, and the changes in the sensor output when the subject changes position can be analyzed according to the model (as described above, for example) to assess the tolerance of the individual to volume loss. Such monitoring and/or analysis can be performed in real time.

Returning to FIG. 2, based on the analysis of the data (whether data collected directly by sensors or derived data, such as CRI, or both) against a model (which might include multiple submodels, such as a model of HE against raw data and a model of HE against CRI), the method 200 can include assessing the effectiveness of hydration of the patient (block 230), based on analysis of the patient's physiological data against the model. As noted above, assessing effectiveness of hydration can include estimating or predicting a number of values, such as the estimated effectiveness, HE, of the hydration effort, the volume, V, of fluid necessary for effective hydration, the probability, $P_f$, that the patient needs fluids, and/or the like.

In some cases, the assessment of the effectiveness of hydration will be based on the analysis of a plurality of measured (or derived) values of a particular physiological parameter (or plurality of parameters). Hence, in some cases, the analysis of the data might be performed on a continuous waveform, either during or after measurement of the waveform with a sensor (or both), and the assessment of the effectiveness can be updated as hydration efforts continue. Further, the amount of fluids added to the patient's blood volume can be measured directly, and these direct measurements (at block 235) can be fed back into the model to update the model and thereby improve performance of the algorithms in the model (e.g., by refining the weights given to different parameters in terms of estimative or predictive value). The updated model can then be used to continue assessing the treatment (in the instant patient and/or in a future patient), as shown by the broken lines on FIG. 2A.

Figure 6:
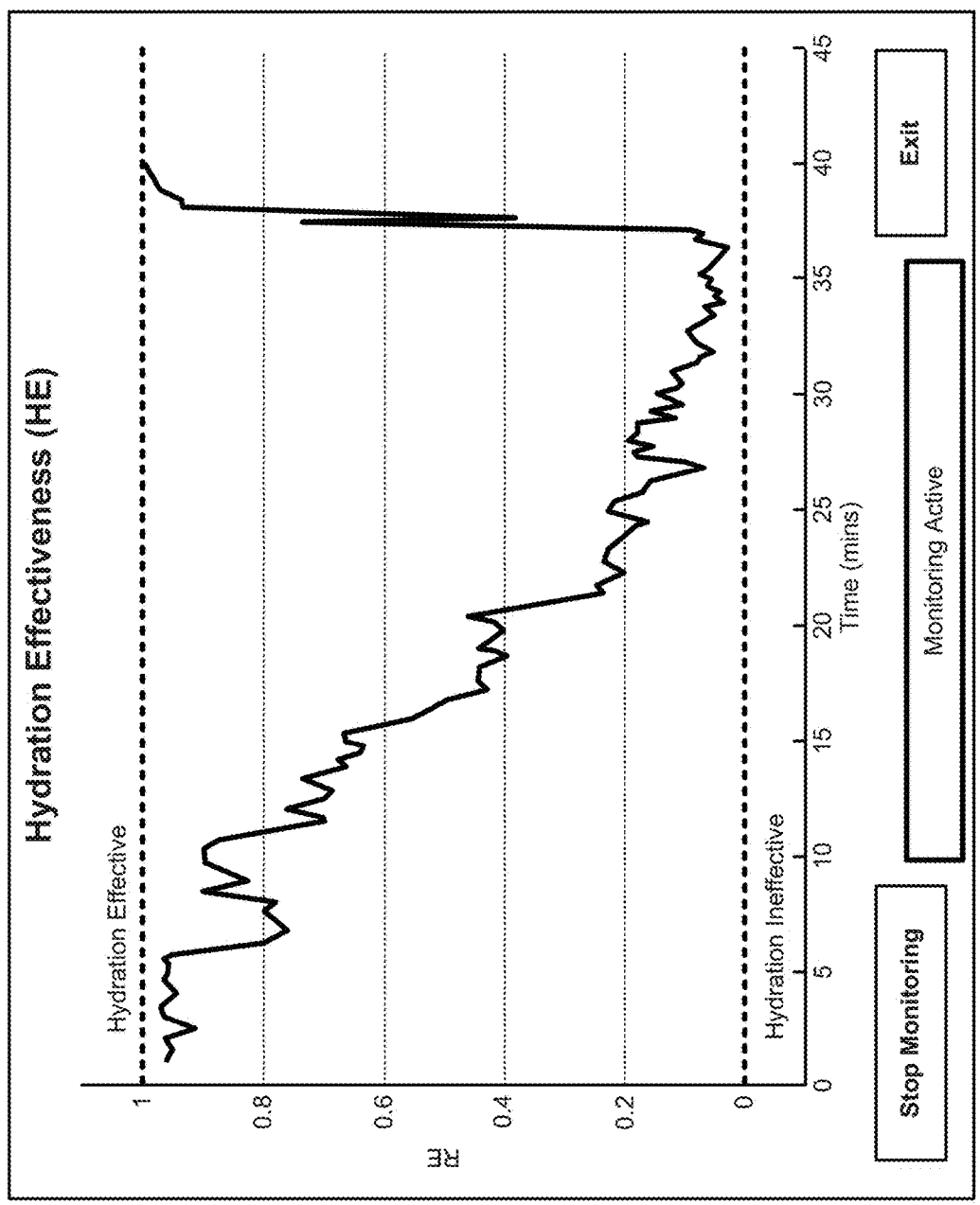
FIGS. 6-8 are exemplary screen captures illustrating display features of a compensatory reserve monitor showing assessments of hydration effectiveness, in accordance with various techniques.

In some cases, the method 200 comprises displaying data (block 240) indicating the assessment of the effectiveness of hydration. In some cases, the data might be displayed on a display of a sensor device (such as the device 105 illustrated by FIG. 1B). Alternatively and/or additionally the data might be displayed on a dedicated machine, such as a compensatory reserve monitor, or on a monitor of a generic computer system. The data might be displayed alphanumerically, graphically, or both. FIGS. 6-8, described below, illustrate several possible exemplary displays of assessments of hydration effectiveness. There are many different ways that the data can be displayed, and any assessments, estimates or predictions generated by the method 200 can be displayed in any desired way, in accordance with various embodiments.

In certain embodiments, the method 200 can include selecting and/or displaying treatment options for the patient (block 245) and/or controlling a therapeutic device (block 250) based on the assessment of the effectiveness of hydration of the patient. For example, a display might indicate to a clinician or the patient himself or herself that the patient is becoming (or has become) dehydrated, that fluid resuscitation therapy should be initiated, an estimated volume of fluid to drink, infuse, or otherwise consume, a drip rate for an IV drip, a flow rate for an IV pump or infuser, or the like. Similarly, the system might be configured to control operation of a therapeutic device, such as dispensing a fluid to drink from an automated dispenser, activating or adjusting the flow rate of an IV pump or infuser, adjusting the drip rate of an IV drip, and/or the like, based on the assessment of the effectiveness of hydration. As another example, certain embodiments might include a water bladder (e.g., a backpack-based hydration pack, such as those available from Camelbak Products LLC) or a water bottle, and the hydration monitor could communicate with and/or control operation of such a dispensing device (e.g., to cause the device to dispense a certain amount of fluid, to cause the device to trigger an audible alarm, etc.).

Further, in certain embodiments, the method 200 can include functionality to help a clinician (or other entity) to monitor hydration, fluid resuscitation and/or blood volume status. For example, in some cases, any measure of effectiveness outside of the normal range (such as a value of $P_f$ higher than a certain threshold value, a value of HE lower than a threshold value, etc.) would set off various alarm conditions, such as an audible alarm, a message to a physician, a message to the patient, an update written automatically to a patient's chart, etc. Such messaging could be accomplished by electronic mail, text message, etc., and a sensor device or monitoring computer could be configured with, e.g., an SMTP client, text messaging client, or the like to perform such messaging.

In some cases, feedback and/or notifications might be sent to a third party, regardless of whether any alarm condition were triggered. For example, a hydration monitor might be configured to send monitoring results (e.g., any of the assessments, estimates and/or predictions described herein) to another device or computer, either for personal monitoring by the patient or for monitoring by another. Examples could include transmitting such alarms or data (e.g., by Bluetooth, NFC, WiFi, etc.) to a wireless phone, wearable device (e.g., smart watch or glasses) or other personal device of the patient, e.g., for inclusion in a health monitoring application. Additionally and/or alternatively, such information could be sent to a specified device or computer (e.g., via any available IP connection), for example to allow a parent to monitor a child's (or a child to monitor an elderly parent's) hydration remotely, to allow a coach to monitor a player's hydration remotely, and/or to allow a superior officer to monitor a soldier's hydration remotely. In some cases (e.g., a coach or superior officer), an application might aggregate results from a plurality of hydration monitors, to allow the supervisor to view (e.g., in a dashboard-type configuration), hydration effectiveness (and/or any other data, such as CRI, blood pressure, etc.) for a group of people. Such a display might employ, for example, a plurality of "fuel gauge" displays, one (or more) for each person in the group, allowing the supervisor to quickly ascertain any unusual results (e.g., based on the color of the gauge, etc.).

Similarly, if an alarm condition were met for another physiological parameter (such as blood pressure, which can be estimated as described in the '171 application, for example), that alarm could trigger an assessment of hydration effectiveness via this the method 200, to determine whether the first alarm condition has merit or not. If not, perhaps there could be an automated silencing of the original alarm condition, since all is well at present. More generally, the assessment techniques could be added to an ecosystem of monitoring algorithms (including without limitation those described in the Related Applications), which would inform one another or work in combination, to inform one another about how to maintain optimal physiological stability.

Figure 4:
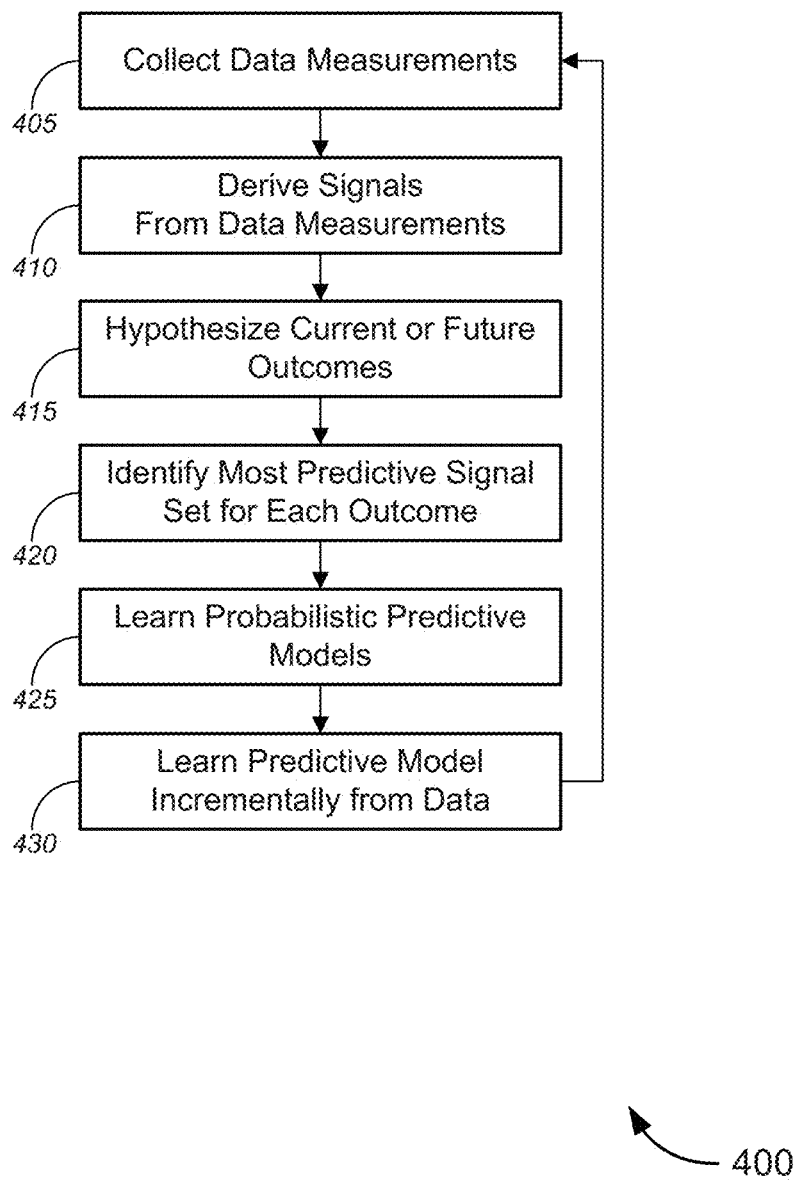
FIG. 4 is a process flow diagram illustrating a method of generating a model of a physiological state, in accordance with various embodiments.

FIG. 4 illustrates a method 400 of employing such a self-learning predictive model (or machine learning) technique, according to some embodiments. In particular, the method 400 can be used to correlate physiological data received from a subject sensor with a measured physiological state. More specifically, with regard to various embodiments, the method 400 can be used to generate a model for assessing, predicting and/or estimating various physiological parameters, such as blood loss volume, effectiveness of hydration or fluid resuscitation efforts, estimated and/or predicted blood pressure, CRI, the probability that a patient is bleeding, a patient's dehydration state, and/or the like, from one or more of a number of different physiological parameters, including without limitation those described above and in the Related Applications.

The method 400 begins at block 405 by collecting raw data measurements that may be used to derive a set of D data signals $s_1, \ldots, s_D$ as indicated at block 410 (each of the data signals s being, in a particular case, input from one or many different physiological sensors). Embodiments are not constrained by the type of measurements that are made at block 405 and may generally operate on any data set. For example, data signals can be retrieved from a computer memory and/or can be provided from a sensor or other input device. As a specific example, the data signals might correspond to the output of the sensors described above (which measure the types of waveform data described above, such as continuous, non-invasive PPG data and/or blood pressure waveform data).

A set of K current or future outcomes $\vec{o}=(o_1, \ldots, o_K)$ is hypothesized at block 415 (the outcomes o being, in this case, past and/or future physiological states, such as probability that fluids are needed, volume of fluid needed for effective hydration or fluid resuscitation, HE, CRI, dehydration state, probability of bleeding, etc.). The method autonomously generates a predictive model M that relates the derived data signals $\vec{s}$ with the outcomes $\vec{o}$. As used herein, "autonomous," means "without human intervention."

As indicated at block 420, this is achieved by identifying the most predictive set of signals $S_k$, where $S_k$ contains at least some (and perhaps all) of the derived signals $s_1, \ldots, s_D$, for each outcome $o_k$, where $k \in \{1, \ldots, K\}$. A probabilistic predictive model $\hat{o}_k = M_k(S_k)$ is learned at block 425, where $\hat{o}_k$ is the prediction of outcome $o_k$ derived from the model $M_k$ that uses as inputs values obtained from the set of signals $S_k$, for all $k \in \{1, \ldots, K\}$. The method 400 can learn the predictive models $\hat{o}_k = M_k(S_k)$ incrementally (block 430) from data that contains example values of signals $s_1, \ldots, s_D$, and the corresponding outcomes $o_1, \ldots, o_K$. As the data become available, the method 400 loops so that the data are added incrementally to the model for the same or different sets of signals $S_k$, for all $k \in \{1, \ldots, K\}$.

While the description above outlines the general characteristics of the methods, additional features are noted. A linear model framework may be used to identify predictive variables for each new increment of data. In a specific embodiment, given a finite set of data of signals and outcomes $\{(\vec{s}_1, \vec{o}_1), (\vec{s}_2, \vec{o}_2), \ldots\}$, a linear model may be constructed that has the form, for all $k \in \{1, \ldots, K\}$, $$\hat{o}_k = f_k(\alpha_0 + \Sigma_{i=1}^d \alpha_i s_i) \quad \text{(Eq. 14)}$$

where $f_k$ is any mapping from one input to one output, and $\alpha_0, \alpha_1, \ldots, \alpha_d$ are the linear model coefficients. The framework used to derive the linear model coefficients may estimate which signals $s, s_1, \ldots, s_d$ are not predictive and accordingly sets the corresponding coefficients $\alpha_0, \alpha_1, \ldots, \alpha_d$ to zero. Using only the predictive variables, the model builds a predictive density model of the data, $\{(\vec{s}_1, \vec{o}_1), (\vec{s}_2, \vec{o}_2), \ldots\}$. For each new increment of data, a new predictive density models can be constructed.

In some embodiments, a prediction system can be implemented that can predict future results from previously analyzed data using a predictive model and/or modify the predictive model when data does not fit the predictive model. In some embodiments, the prediction system can make predictions and/or to adapt the predictive model in real-time. Moreover, in some embodiments, a prediction system can use large data sets not only to create the predictive model, but also predict future results as well as adapt the predictive model.

In some embodiments, a self-learning, prediction device can include a data input, a processor and an output. Memory can include application software that when executed can direct the processor to make a prediction from input data based on a predictive model. Any type of predictive model can be used that operates on any type of data. In some embodiments, the predictive model can be implemented for a specific type of data. In some embodiments, when data is received the predictive model can determine whether it understands the data according to the predictive model. If the data is understood, a prediction is made and the appropriate output provided based on the predictive model. If the data is not understood when received, then the data can be added to the predictive model to modify the model. In some embodiments, the device can wait to determine the result of the specified data and can then modify the predictive model accordingly. In some embodiments, if the data is understood by the predictive model and the output generated using the predictive model is not accurate, then the data and the outcome can be used to modify the predictive model. In some embodiments, modification of the predictive model can occur in real-time.

Particular embodiments can employ the tools and techniques described in the Related Applications in accordance with the methodology described herein perform the functions of a cardiac reserve monitor, a wrist-wearable sensor device, and/or a monitoring computer, as described herein (the functionality of any or all of which can be combined in a single, integrated device, in some embodiments). These functions include, but are not limited to, assessing fluid resuscitation of a patient, assessing hydration of a patient, monitoring, estimating and/or predicting a subject's (including, without limitation, a patient's) current or future blood pressure and/or compensatory reserve, estimating and/or determining the probability that a patient is bleeding (e.g., internally) and/or has been bleeding, recommending treatment options for such conditions, and/or the like. Such tools and techniques include, in particular, the systems (e.g., computer systems, sensors, therapeutic devices, etc.) described in the Related Applications, the methods (e.g., the analytical methods for generating and/or employing analytical models, the diagnostic methods, etc.), and the software programs described herein and in the Related Applications, which are incorporated herein by reference.

Figure 5:
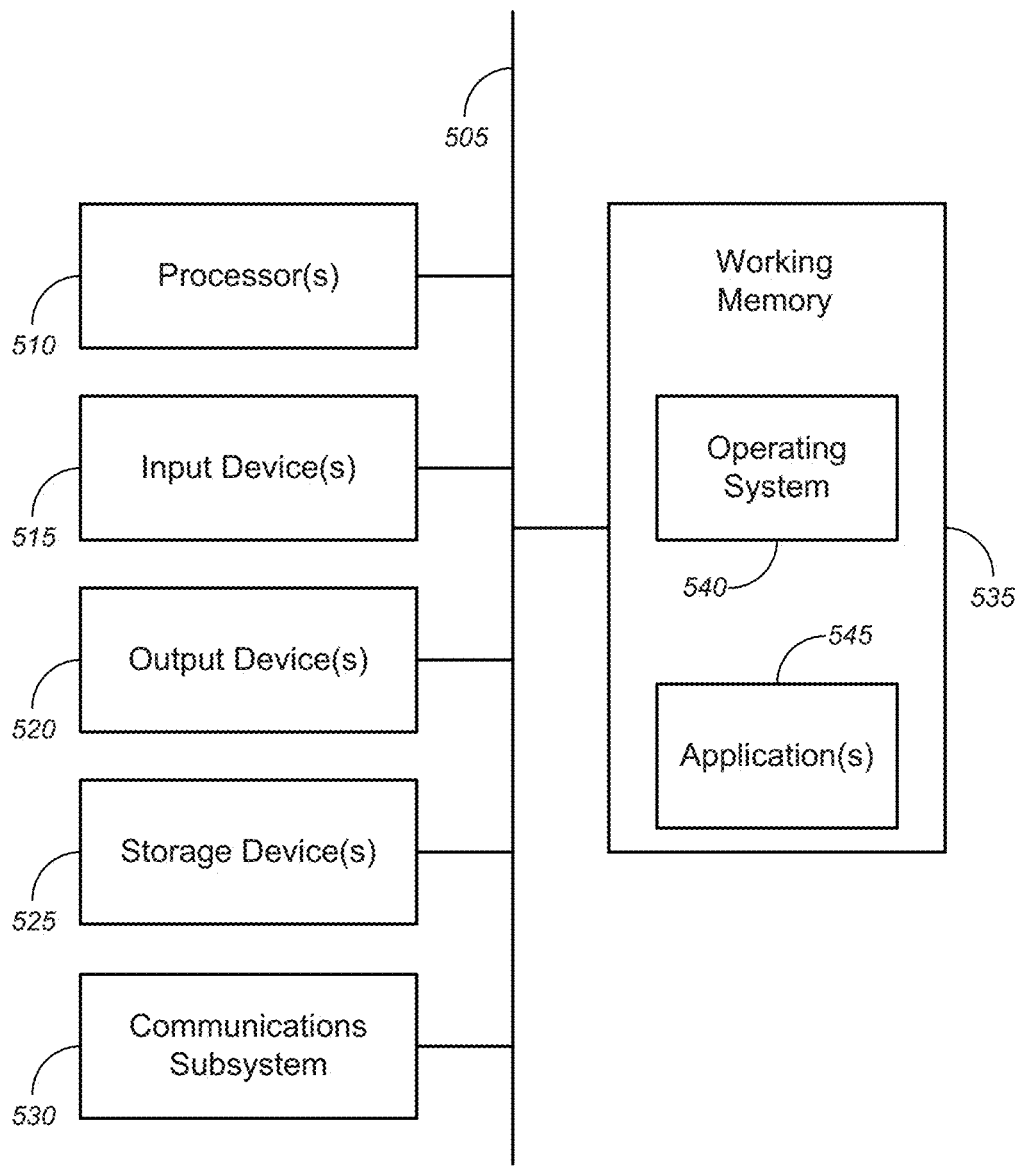
FIG. 5 is a generalized schematic diagram illustrating a computer system, in accordance with various embodiments.

Hence, FIG. 5 provides a schematic illustration of one embodiment of a computer system 500 that can perform the methods provided by various other embodiments, as described herein, and/or can function as a monitoring computer, CRI monitor, processing unit of sensor device, etc. It should be noted that FIG. 5 is meant only to provide a generalized illustration of various components, of which one or more (or none) of each may be utilized as appropriate. FIG. 5, therefore, broadly illustrates how individual system elements may be implemented in a relatively separated or relatively more integrated manner.

The computer system 500 is shown comprising hardware elements that can be electrically coupled via a bus 505 (or may otherwise be in communication, as appropriate). The hardware elements may include one or more processors 510, including, without limitation, one or more general-purpose processors and/or one or more special-purpose processors (such as digital signal processing chips, graphics acceleration processors, and/or the like). In general, embodiments can employ as a processor 510 any device (or combination of devices) that can operate to execute instructions to perform functions as described herein. Merely by way of example, and without limitation, any microprocessor (also sometimes referred to as a central processing unit, or "CPU") can be used as the processor 510, including, without limitation, one or more complex instruction set computing ("CISC") microprocessors, such as the single core and multicore processors available from Intel Corporation™ and others, such as Intel's X86 platform, including, e.g., the Pentium™, Core™, and Xeon™ lines of processors. Additionally and/or alternatively, reduced instruction set computing ("RISC") microprocessors, such as the IBM Power™ line of processors, processors employing chip designs by ARM Holdings™, and others can be used in many embodiments. In further embodiments, a processor 510 might be a microcontroller, embedded processor, embedded system, system on a chip ("SoC") or the like.

As used herein, the term "processor" can mean a single processor or processor core (of any type) or a plurality of processors or processor cores (again, of any type) operating individually or in concert. Merely by way of example, the computer system 500 might include a general-purpose processor having multiple cores, a digital signal processor, and a graphics acceleration processor. In other cases, the computer system 500 might include a CPU for general purpose tasks and one or more embedded systems or microcontrollers, for example, to run real-time functions. The functionality described herein can be allocated among the various processors or processor cores as needed for specific implementations. Thus, it should be noted that, while various examples of processors have been described herein for illustrative purposes, these examples should not be considered limiting.

The computer system 500 can also include (or be in communication with) one or more input devices 515, which can include, without limitation, a mouse, a keyboard, a touch screen, a trackpad, and/or the like; and one or more output devices 520, which can include, without limitation, a display device, a printer and/or the like. The computer system 500 may further include (and/or be in communication with) one or more storage devices 525, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including, without limitation, various file systems, database structures, and/or the like.

The computer system 500 might also include a communications subsystem 530, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 530 may permit data to be exchanged with a network (such as the network described below, to name one example), with other computer systems, and/or with any other devices described herein. In many embodiments, the computer system 500 will further comprise a working memory 535, which can include a RAM or ROM device, as described above.

The computer system 500 also may comprise software elements, shown as being currently located within the working memory 535, including an operating system 540, device drivers, executable libraries, and/or other code, such as one or more application programs 545, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 525 described above. In some cases, the storage medium might be incorporated within a computer system, such as the system 500. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer system 500 and/or might take the form of source and/or installable code, which, upon compilation and/or installation on the computer system 500 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 500) to perform methods in accordance with various embodiments of the invention. According to a set of embodiments, some or all of the procedures of such methods are performed by the computer system 500 in response to processor 510 executing one or more sequences of one or more instructions (which might be incorporated into the operating system 540 and/or other code, such as an application program 545) contained in the working memory 535. Such instructions may be read into the working memory 535 from another computer readable medium, such as one or more of the storage device(s) 525. Merely by way of example, execution of the sequences of instructions contained in the working memory 535 might cause the processor(s) 510 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 500, various computer readable media might be involved in providing instructions/code to processor(s) 510 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 525. Volatile media includes, without limitation, dynamic memory, such as the working memory 535. In some alternative embodiments, a computer readable medium may take the form of transmission media, which includes, without limitation, coaxial cables, copper wire and fiber optics, including the wires that comprise the bus 505, as well as the various components of the communication subsystem 530 (and/or the media by which the communications subsystem 530 provides communication with other devices). In an alternative set of embodiments, transmission media can also take the form of waves (including, without limitation, radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, a RAM, ROM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 500. These signals, which might be in the form of electromagnetic signals, acoustic signals, optical signals and/or the like, are all examples of carrier waves on which instructions can be encoded, in accordance with various embodiments of the invention.

The communications subsystem 530 (and/or components thereof) generally will receive the signals, and the bus 505 then might carry the signals (and/or the data, instructions, etc. carried by the signals) to the working memory 535, from which the processor(s) 505 retrieves and executes the instructions. The instructions received by the working memory 535 may optionally be stored on a storage device 525 either before or after execution by the processor(s) 510.

FIGS. 6-8 illustrate exemplary screen captures from a display device of a compensatory reserve monitor, showing various features that can be provided by one or more embodiments. Similar screens could be shown by other monitoring devices, such as a display of a wrist-wearable sensor device, a display of a monitoring computer, and/or the like. While FIGS. 6-8 use HE as an example condition for illustrative purposes, other embodiments might also display values for the volume, V, the volume of fluid necessary for effective hydration, or the probability, $P_f$, that the patient needs fluid (including additional fluid, if hydration efforts already are is underway).

FIG. 6 illustrates an exemplary display 600 of a compensatory reserve monitor implementation where a normalized hydration effectiveness ("HE") of "1" implies that the hydration efforts have been or are completely effective, and "0" implies that the hydration efforts have been or are completely ineffective. Values in between "0" and "1" imply a continuum of effectiveness.

Figure 7A:
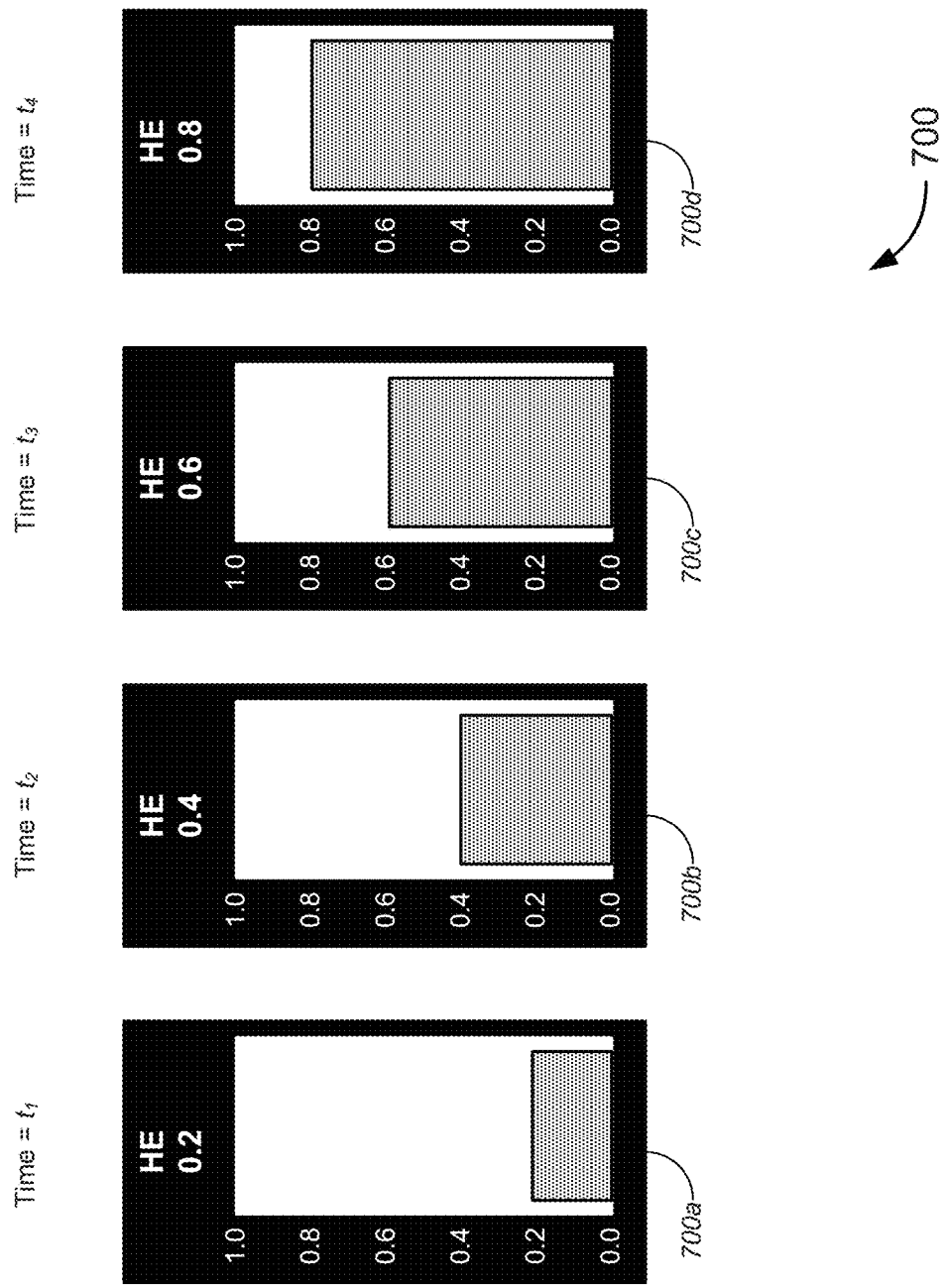
Figure 8:
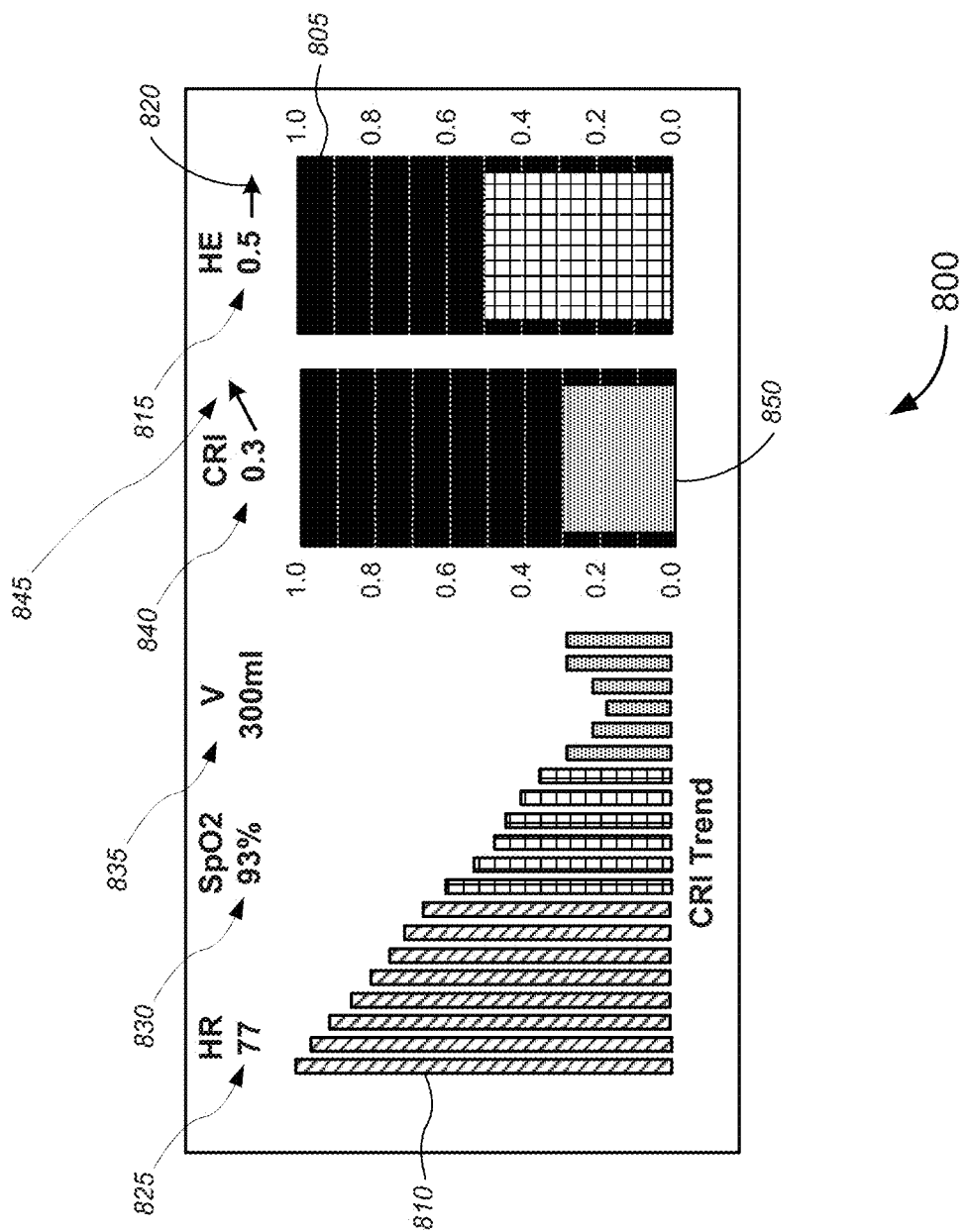

FIG. 7A illustrates four screen captures 700 of a display of a compensatory reserve monitor implementation that displays HE as a "fuel gauge" type bar graph for a person undergoing central volume blood loss and subsequent hydration efforts. While FIG. 6 illustrates a trace of HE over time, the bar graphs of FIG. 7A provide snapshots of HE at the time of each screen capture. (In the illustrated implementation, the bar graphs are continuously and/or periodically updated, such that each bar graph could correspond to a particular position on the X-axis of FIG. 6.)

Figure 7B:
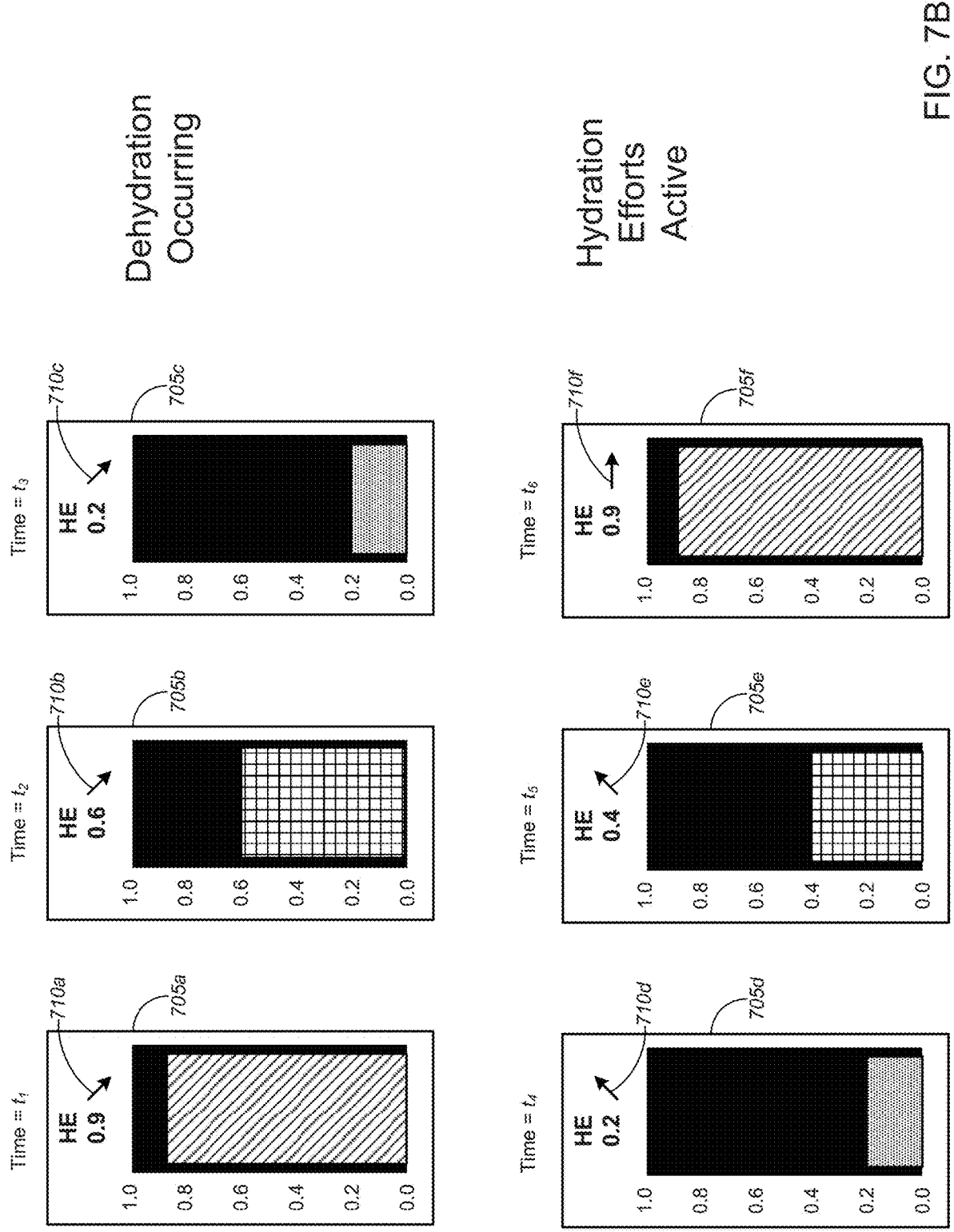

A variety of additional features are possible. Merely by way of example, FIG. 7B illustrates similar "fuel gauge" type displays, but the displays 705 of FIG. 7B feature bars of different colors—for example, green (illustrated by diagonal cross-hatching), yellow (illustrated by a checked or checkered pattern), and red (illustrated by gray shading) corresponding to different levels of HE, along with arrows 710 indicating trending in the HE values (e.g., rising, declining, or remaining stable).

In some embodiments, such a "fuel gauge" display (or other indicator of HE and/or different physiological parameters) can be incorporated in a more comprehensive user interface. Merely by way of example, FIG. 8 illustrates an exemplary display 800 of a monitoring system. The display 800 includes a graphical, color-coded "fuel gauge" type display 805 of the current estimated HE (similar to the displays illustrated by FIG. 7B), along with a historical display 810 of recent CRI estimates; in this example, each bar on the historical display 810 might correspond to an estimate performed every minute, but different estimate frequencies are possible, and in some embodiments, the operator can be given the option to specify a different frequency. In the illustrated embodiment, the display 800 also includes numerical display 815 of the current HE as well as a trend indicator 820 (similar to that indicated above).

In particular embodiments, the display 800 can include additional information (and, in some cases, the types of information displayed and/or the type of display can be configured by the operator). For instance, the exemplary display 800 includes an indicator 825 of the patient's current heart rate and an indicator 830 of the patient's blood oxygen saturation level (SpO2). The exemplary display 800 also includes an indicator of the estimated volume, V, necessary for effective hydration, as well as a numerical indicator 840, a trend indicator 845, and a similar color coded "fuel gauge" display 850 of the current set of CRI values. Other monitored parameters might be displayed as well, such as an ECG tracing, blood pressure, probability of bleeding estimates, and/or the like.

Exemplary Clinical Studies

In a clinical study performed by the inventors, accurate guidance of resuscitation volume needs in trauma patients were examined. As background, hemorrhage is the second leading cause of trauma-related death and the most common cause of preventable death on the battlefield. Accurate guidance for fluid resuscitation of injured warfighters is critical to improving patient outcomes. In this study, three new algorithms for guiding fluid resuscitation were evaluated. The first was estimating Fluid Volume Requirements ("FVR Algorithm"), which monitors the patient's photoplethysmogram ("PPG") signal as fluid is administered, and directly estimates amount of whole blood (in milliliters (mL)) needed. The second was Detection of Ongoing Fluid Loss ("DOFL Algorithm"), which monitors a patient's PPG signal and directly identifies whether the patient is experiencing ongoing blood loss. The third was Rapid Estimation of Immediate Fluid Requirements ("REIFR Algorithm"), which monitors the patient's PPG signal and flags the need for additional fluid (this classification is made within one minute of the start of monitoring, and gives real-time indication of over- and under-resuscitation).

Figure 9A:
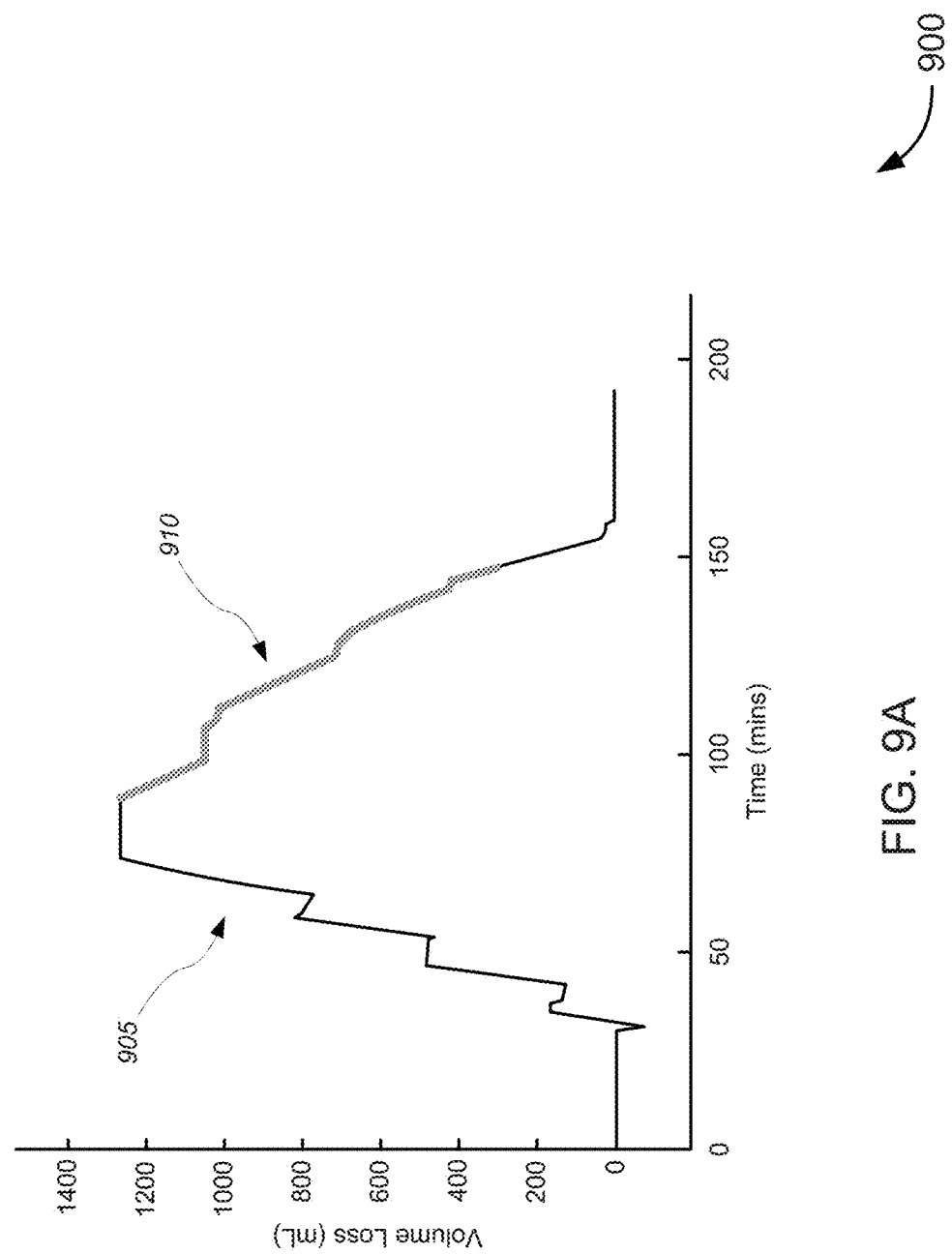
FIG. 9A is a graphical diagram depicting an example a resuscitation interval overlaid over a blood draw profile, in accordance with various embodiments.
Figure 9B:
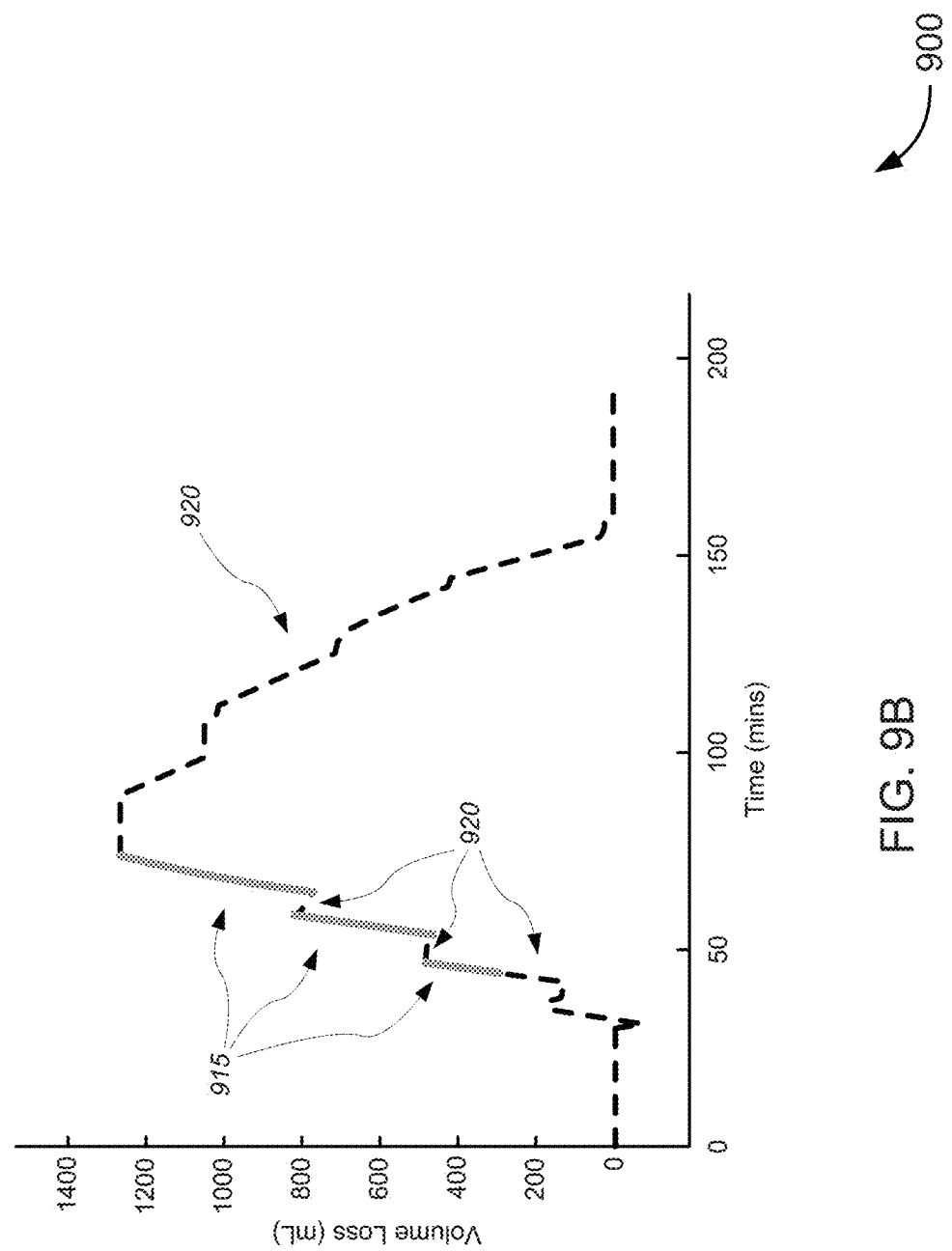
FIG. 9B is a graphical diagram depicting intervals of ongoing bleeding between periods of non-ongoing bleeding during the example blood draw profile of FIG. 9A, in accordance with various embodiments.
Figure 9C:
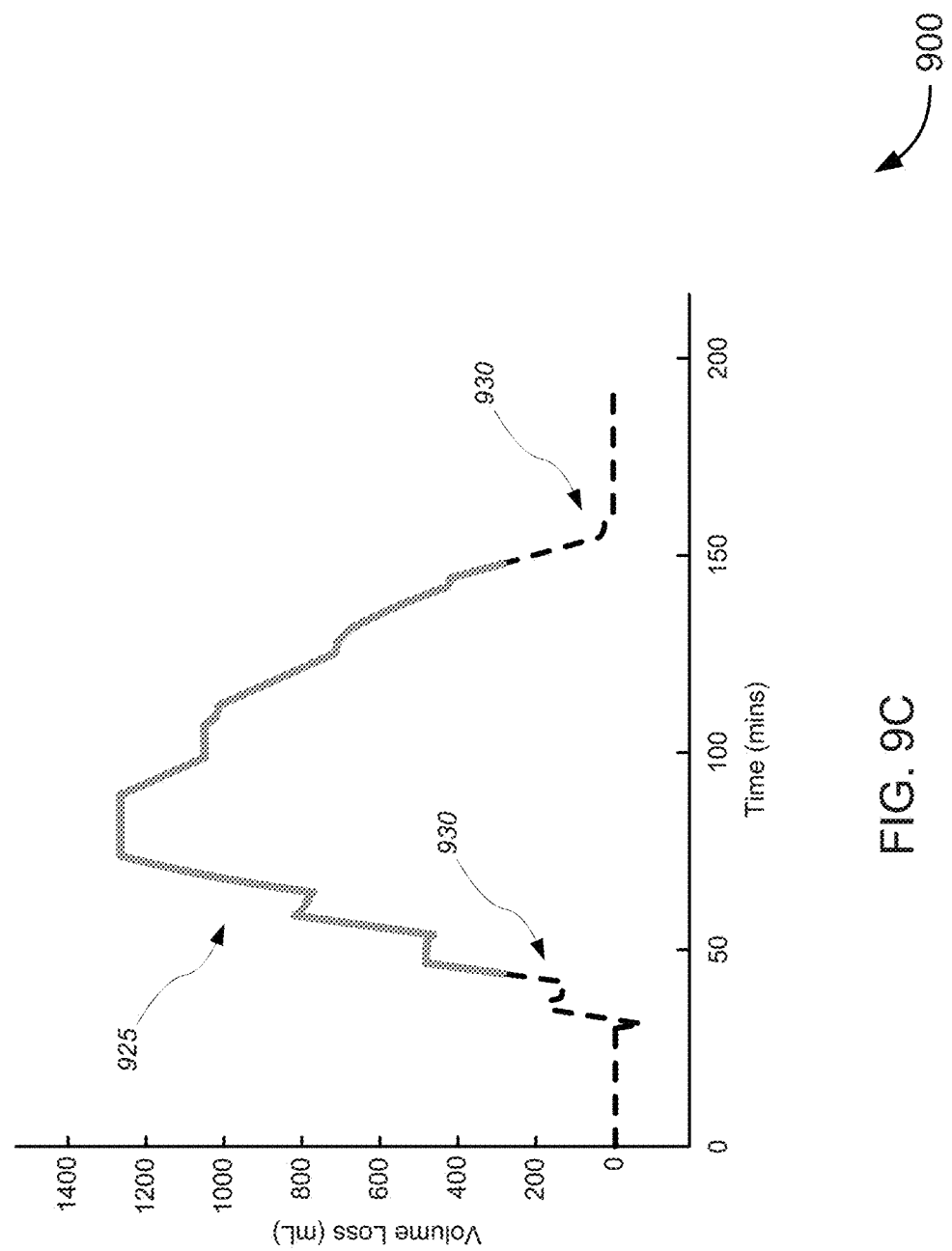
FIG. 9C is a graphical diagram depicting periods during which fluid is needed and periods during which fluid is not needed during the example blood draw profile of FIG. 9A, in accordance with various embodiments.

In this study, 42 healthy volunteers (ages 19 to 36, 18 females and 24 males) underwent stepwise removal and replacement of approximately 20% of total blood volume (15 mL/Kg male; 13 mL/Kg female) while in the supine position at rest. A large bore IV was placed for blood removal and replacement. The blood was removed in 2-6 steps (with total blood removal of 578 mL to 1470 mL). Resuscitation was immediately given if the subject experienced symptoms due to blood loss, defined as a systolic blood pressure <80 mmHg or MAP 30% below baseline. After blood removal was complete, the removed volume was reinfused. Subjects were monitored continuously with the Nonin 9560 fingertip pulse oximeter. PPG signals were recorded and synchronized with blood draws and reinfusion. The FVR algorithm was applied to 5-minute moving time windows during the resuscitation (blood reinfusion, shown as the thick gray curve 910 overlaid on the blood draw profile 905 in FIG. 9A) period, and provided real-time estimates of additional volume required (in mL) to fully replace the fluid removed. Ongoing fluid loss was the blood draw period in the study (shown as the thick gray line segments 915 overlaid on the non-ongoing periods of the blood draw period (shown by the dashed line curve 920) in FIG. 9B). The DOFL algorithm was applied to 5-minute moving time windows during the study and gave real-time classification of ongoing bleeding. Finally, the subject was classified as needing fluid once 5% volume loss was achieved. FIG. 9C depicts the period during which fluid is needed (shown by thick gray line 925 overlaid on the dashed line segments 930, which indicates that fluid is not needed). The REIFR Algorithm was applied to 1-minute moving time windows and gave real-time classification of (yes/no determinations of) needing fluids.

Figure 10A:
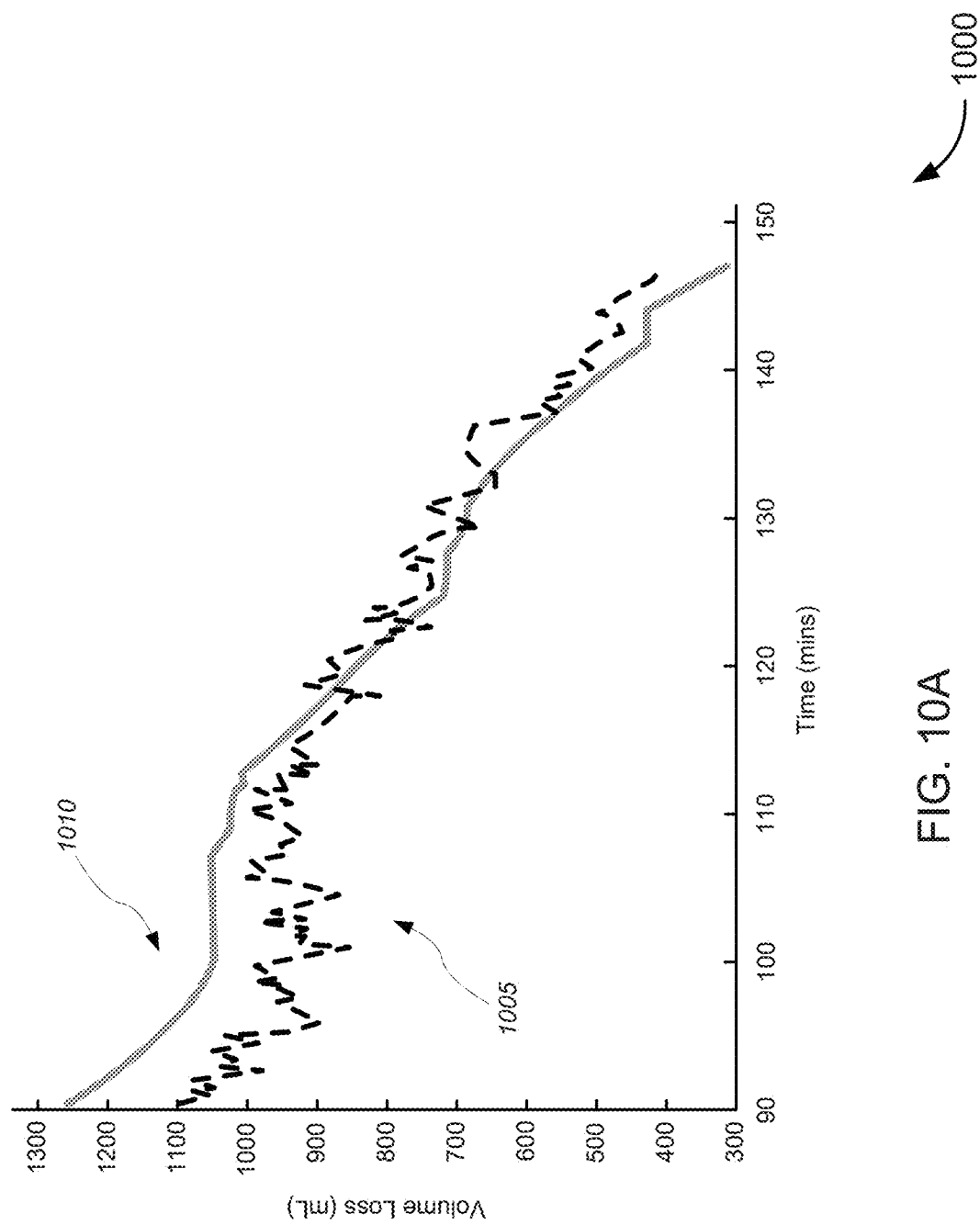
FIGS. 10A-10C are graphical diagrams depicting comparison between actual or reference blood draw resuscitation volume required versus estimated blood resuscitation volume needed (as calculated using the Fluid Volume Requirements ("FVR") Algorithm) for each of three subjects, in accordance with various embodiments.
Figure 10B:
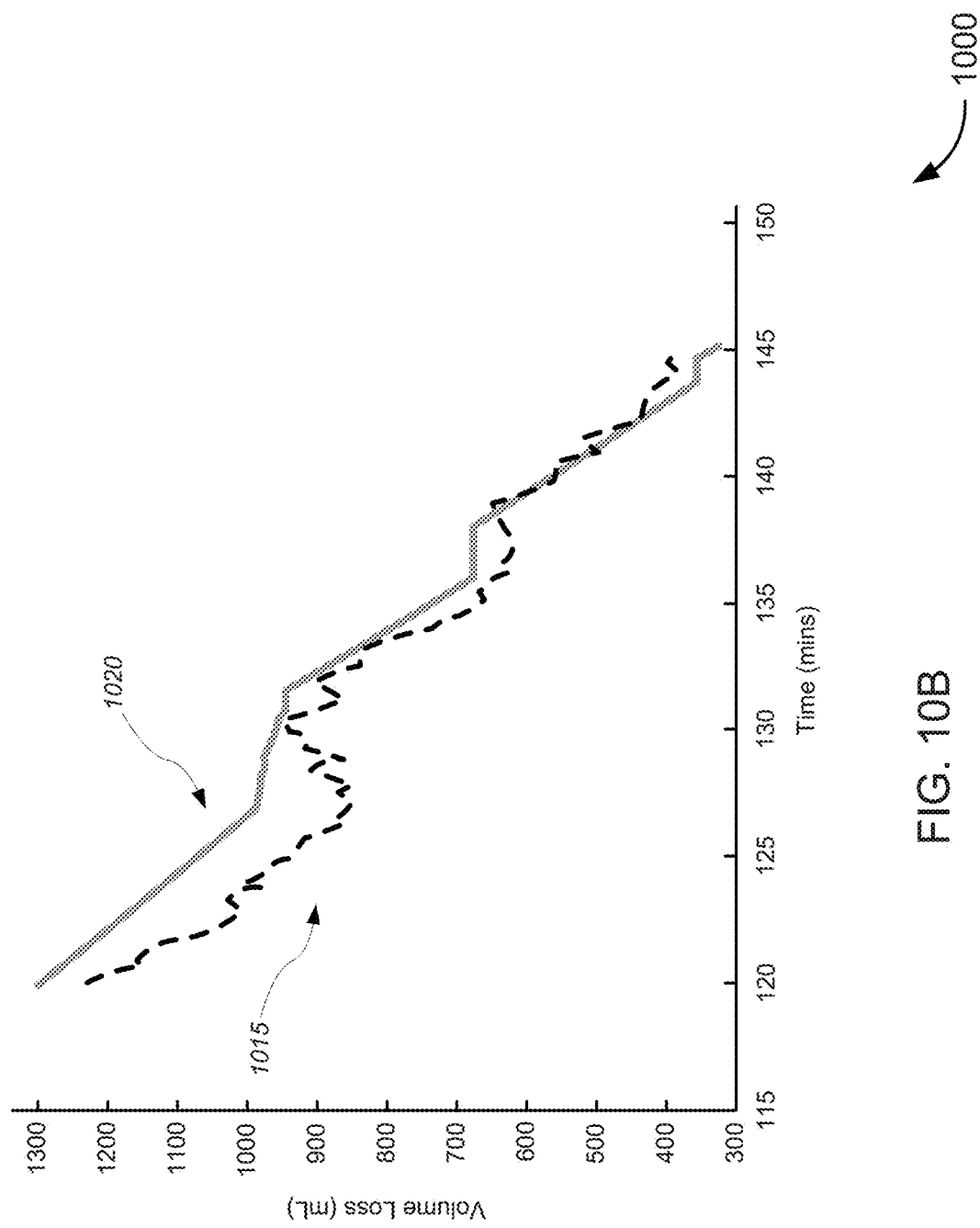
Figure 10C:
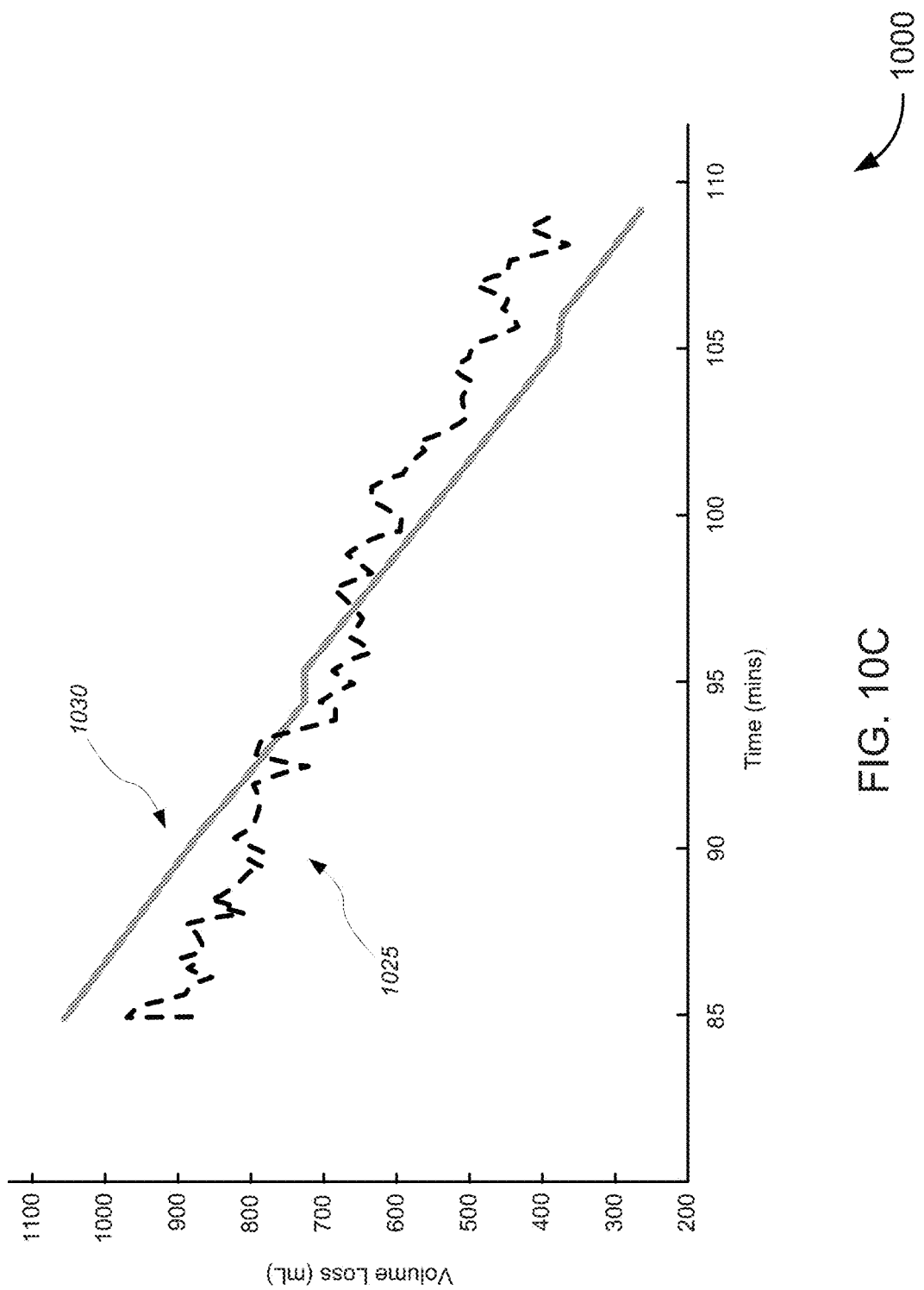

Regarding the results, the FVR Algorithm achieved a RMS error of <50 mL in estimated blood volume requirements. Experimental results from three subjects are shown in FIGS. 10A-10C (collectively, "FIG. 10"), where the dash line curve 1005 (FIG. 10A), 1015 (FIG. 10B), and 1025 (FIG. 10C) each shows the FVR monitor's estimate of fluid requirements, while the actual fluid requirements are shown by the thick gray curve 1010 (FIG. 10A), 1020 (FIG. 10B), and 1030 (FIG. 10C), for patients 1, 17, and 10, respectively.

Figure 11:
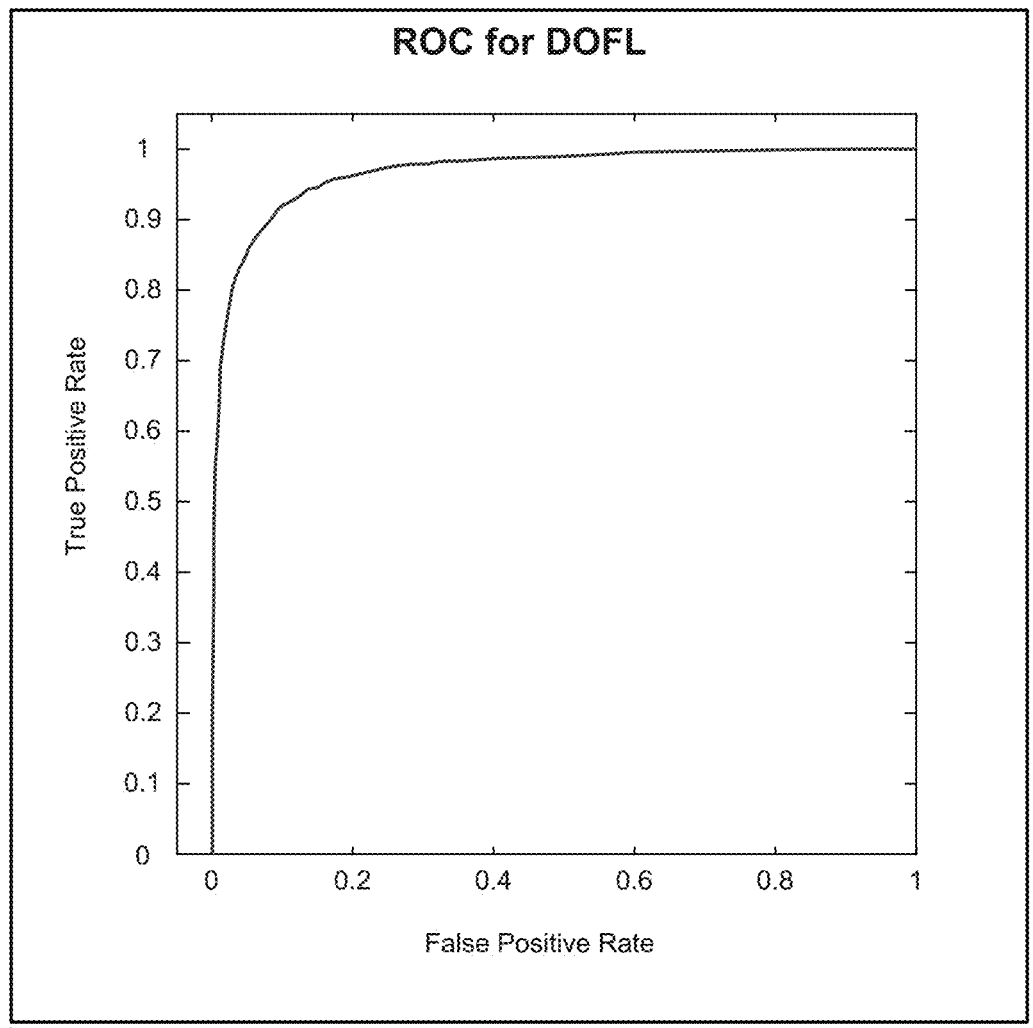
FIG. 11 is a graphical diagram illustrating receiver operating characteristic ("ROC") area under the curve ("AUC") for Detection of Ongoing Fluid Loss ("DOFL") Algorithm, in accordance with various embodiments.
Figure 12:
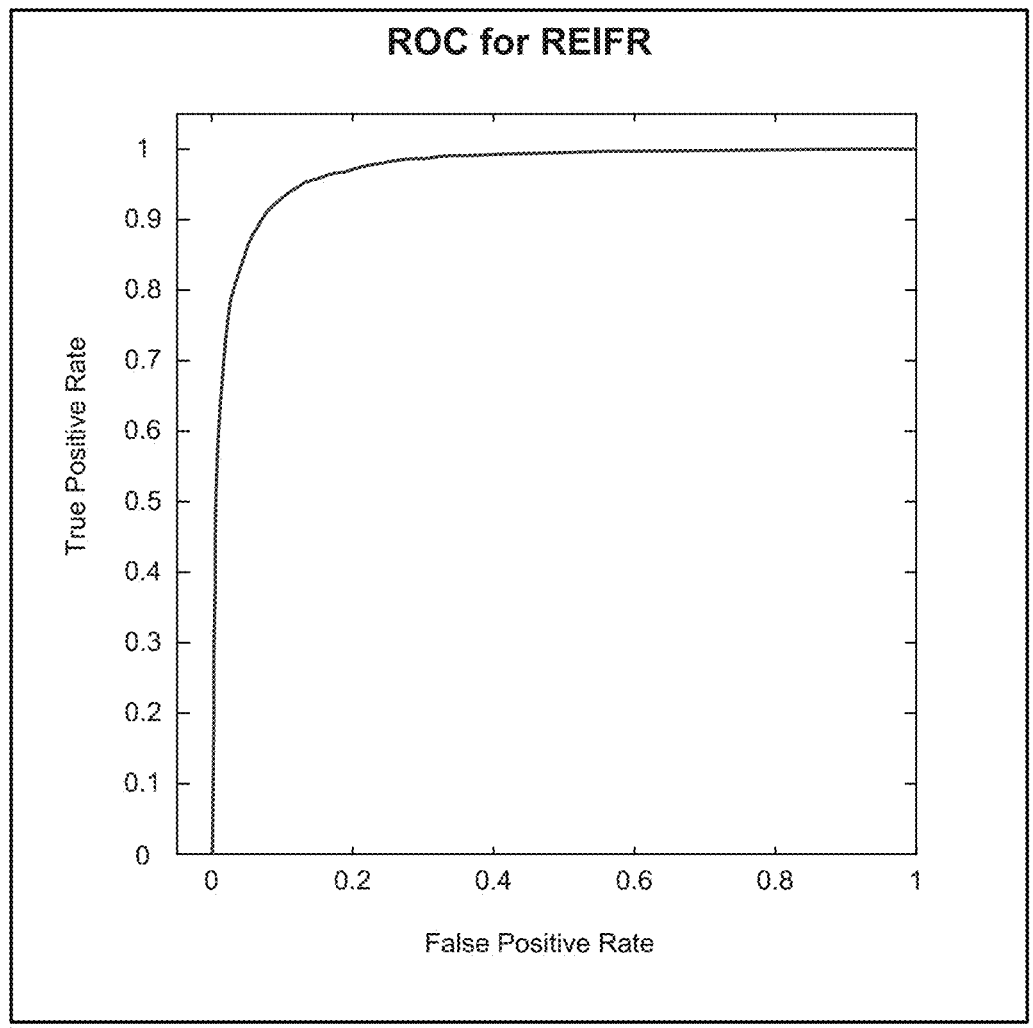
FIG. 12 is a graphical diagram illustrating receiver operating characteristic ("ROC") area under the curve ("AUC") for Rapid Estimation of Immediate Fluid Requirements ("REIFR") Algorithm, in accordance with various embodiments.

Both the DOFL and REIFR Algorithms achieved ROC area under the curve of better than 0.9 (sensitivity and specificity of >0.9) in identifying ongoing bleeding and flagging when no additional fluids were needed. For example, the DOFL Algorithm achieved ROC area under the curve of 0.9697, sensitivity of 0.9192, and specificity of 0.9028 in identifying ongoing bleeding, as shown in FIG. 11. The REIFR Algorithm achieved ROC area under the curve of 0.9724, sensitivity of 0.9330, and specificity of 0.9000 in determining when no additional fluids were needed, as shown in FIG. 12.

In sum, the three algorithms for monitoring fluid resuscitation were evaluated on subjects undergoing 20% blood volume loss. These algorithms showed accurate results in estimation of blood volume requirements, classifying ongoing bleeding, and classifying when no additional whole blood was needed. These algorithms can be implemented on standard medical monitors ranging from the Nonin 9550 used by medics, to monitors used in hospitals, and/or the like.

CONCLUSION

This document discloses novel tools and techniques for estimating hydration effectiveness, fluid resuscitation effectiveness, compensatory reserve and similar physiological states. While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A hydration monitor, comprising:
one or more sensors to obtain physiological data from a patient, wherein the physiological data is cardiovascular data of the patient; and
a computer system in communication with the one or more sensors, the computer system comprising:
one or more processors; and
a computer readable medium in communication with the one or more processors, the computer readable medium having encoded thereon a set of instructions that, when executed by the one or more processors, causes the computer system to:
receive a first set of physiological data from the one or more sensors at a first time in relation to a physical perturbation of the patient;
calculate a first set of compensatory reserve index ("CRI") values of the patient based on a comparison of the first set of physiological data to a model comprising a plurality of waveforms of reference data, each waveform of the plurality of waveforms corresponding to a respective CRI value determined from a ratio of intravascular volume loss at time t and intravascular volume loss at hemodynamic decompensation,
wherein the first set of physiological data includes waveform data of the patient at the first time, wherein waveform data of the patient at the first time includes one or more first patient waveforms,
wherein comparing the first set of physiological data against the model comprises comparing the waveform data of the patient against the plurality of waveforms of reference data, and determining a similarity between a respective first patient waveform of the one or more first patient waveforms and each of one or more waveforms of the plurality of waveforms of reference data individually, and
wherein calculating a respective first CRI value of the first set of CRI values of the patient corresponding to the respective first patient waveform is based at least in part on respective similarities of the respective first patient waveform to each of the one or more waveforms of the plurality of waveforms of reference data individually;

receive a second set of physiological data from the one or more sensors at a second time in relation to the physical perturbation of the patient;

calculate a second set of CRI values of the patient based on a comparison of the second set of physiological data to the model, wherein the second set of physiological data includes waveform data of the patient at the second time;

based at least in part on a change between the first and second sets of CRI values, estimate a hydration state of the patient, wherein the change between the first and second sets of CRI values is compared against a CRI model separate from the model comprising the plurality of waveforms of reference data, wherein the CRI model relates changes in CRI value to the hydration state of the patient; and display on a display device, an estimate of the hydration state of the patient.

2. The hydration monitor of claim 1, wherein the one or more sensors comprise a finger cuff comprising a fingertip photoplethysmograph, and wherein the computer system comprises a wrist unit in communication with the fingertip photoplethysmograph, the wrist unit further comprising a wrist strap.

3. The hydration monitor of claim 1, wherein estimating a hydration state of the patient comprises determining whether the patient needs more fluids.

4. The hydration monitor of claim 3, wherein determining whether the patient needs more fluids comprises determining whether the patient has an increase in fluid requirements.

5. The hydration monitor of claim 3, wherein determining whether the patient needs more fluids comprises estimating how much fluid is needed, based at least in part on how much fluid the patient has received between the first time and the second time in relation to the physical perturbation of the patient.

6. A method, comprising:
monitoring, with one or more sensors, physiological data of a patient, wherein the physiological data is cardiovascular data of the patient;

receiving a first set of physiological data from the one or more sensors at a first time in relation to a physical perturbation of the patient;

calculating a first set of compensatory reserve index ("CRI") values of the patient based on a comparison of the first set of physiological data to a model comprising a plurality of waveforms of reference data, each waveform of the plurality of waveforms corresponding to a respective CRI value determined from a ratio of intravascular volume loss at time t and intravascular volume loss at hemodynamic decompensation, wherein the first set of physiological data includes waveform data of the patient at the first time, wherein waveform data of the patient at the first time includes one or more first patient waveforms, wherein comparing the first set of physiological data against the model comprises comparing the waveform data of the patient against the plurality of waveforms of reference data, and determining a similarity between a respective first patient waveform of the one or more first patient waveforms and each of one or more waveforms of the plurality of waveforms of reference data individually, and wherein calculating a respective first CRI value of the first set of CRI values of the patient corresponding to the respective first patient waveform is based at least in part on respective similarities of the respective first patient waveform to each of the one or more waveforms of the plurality of waveforms of reference data individually;

receiving a second set of physiological data from the one or more sensors at a second time in relation to the physical perturbation of the patient;

calculating a second set of CRI values of the patient based on a comparison of the second set of physiological data to the model, wherein the second set of physiological data includes waveform data of the patient at the second time;

based at least in part on a change between the first and second sets of CRI values, estimating a physiological state of the patient, wherein the change between the first and second sets of CRI values is compared against a CRI model separate from the model comprising the plurality of waveforms of reference data, wherein the CRI model relates changes in CRI value to the physiological state of the patient; and displaying on a display device, an estimate of the physiological state of the patient.

7. The method of claim 6, wherein the physical perturbation of the patient comprises performance of an exercise.

8. The method of claim 7, wherein the exercise comprises a squat exercise.

9. The method of claim 7, wherein the exercise comprises a sit-up exercise.

10. The method of claim 6, wherein the physical perturbation comprises delivery of fluid to the patient.

11. The method of claim 6, wherein the physical perturbation comprises introduction of positive or negative pressure to an airway of the patient.

12. The method of claim 6, wherein the physiological state is a hydration state of the patient.

13. The method of claim 6, wherein the physiological state is an estimated point of cardiovascular collapse of the patient.

14. The method of claim 6, wherein the ratio of intravascular volume loss at time t and intravascular volume loss at hemodynamic decompensation is determined by the following formula:

$$CRI(t) = 1 - \frac{BLV(t)}{BLV_{HDD}},$$

where CRI(t) is the compensatory reserve index at time t, BLV(t) is an intravascular volume loss of the patient at time t, and $BLV_{HDD}$ is an intravascular volume loss of the patient at a point of hemodynamic decompensation.

15. The method of claim 14, wherein the physiological data comprises waveform data, and wherein estimating a set of CRI values of the patient comprises comparing the waveform data with one or more sample waveforms generated by exposing each of one or more test subjects to a state of hemodynamic decompensation or near hemodynamic decompensation or to a series of states progressing towards hemodynamic decompensation, and monitoring physiological data of the test subjects.

16. The method of claim 14, wherein determining the similarity between the respective first patient waveform and each of the one or more waveforms of the plurality of waveforms of reference data individually further comprises:
producing one or more similarity coefficients, each similarity coefficient of the one or more similarity coefficients expressing a respective similarity between the respective first patient waveform and each of the one or more waveforms of the plurality of waveforms of reference data individually;

wherein estimating the respective first CRI value of the patient corresponding to the respective first patient waveform further comprises:

normalizing each of the one or more similarity coefficients for each of the one or more waveforms of the plurality of waveforms of reference data; and summing each respective CRI value corresponding to a respective individual waveform of the one or more waveforms of the plurality of waveforms of reference data, weighted by the normalized similarity coefficient corresponding to the respective individual waveform of the one or more waveforms of the plurality of waveforms of reference data, for each of the one or more waveforms of the plurality of waveforms of reference data; and determining, for the respective first patient waveform, an estimated respective first CRI value for the patient.

17. The method of claim 6, wherein at least one of the one or more sensors comprises at least one of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, or an electronic stethoscope.

18. The method of claim 6, wherein the physiological data comprises blood pressure waveform data.

19. The method of claim 6, wherein the physiological data comprises plethysmograph waveform data.

20. The method of claim 6, wherein the physiological data comprises photoplethysmograph ("PPG") waveform data.

21. The method of claim 6, further comprising:

generating the model comprising the plurality of waveforms of reference data.

22. The method of claim 6, wherein generating the model comprising the plurality of waveforms of reference data further comprises:

receiving data pertaining to one or more physiological parameters of a test subject to obtain a plurality of physiological data sets;

directly measuring one or more physiological states of the test subject with a reference sensor to obtain a plurality of physiological state measurements; and correlating the received data with the physiological state measurements of the test subject.

23. The method of claim 22, wherein the one or more physiological states comprises one or more states comprising at least one of reduced circulatory system volume, blood loss, added fluids to blood volume, dehydration, hydration state, cardiovascular collapse, near-cardiovascular collapse, euvolemia, or hypervolemia.

24. The method of claim 22, wherein correlating the received data with the physiological state measurements of the test subject comprises:

identifying a most predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter of the physiological data of the test subject, and wherein each of the one or more outcomes $o_k$ represents a physiological state measurement of the one or more physiological states respectively;

autonomously learning a set of probabilistic predictive models $\hat{o}_k = M_k(S_k)$, where $\hat{o}_k$ is a prediction of outcome $o_k$ derived from a model $M_k$ that uses as inputs values obtained from the most predictive set of signals $S_k$; and repeating the operation of autonomously learning incrementally from data that contains examples of values of signals $s_1, s_2, \ldots, s_D$ and corresponding outcomes $o_1, o_2, \ldots, o_K$.

25. The method of claim 6, wherein estimating a physiological state of the patient comprises estimating a hydration state of the patient and determining whether the patient needs more fluids.

26. The method of claim 25, wherein determining whether the patient needs more fluids comprises determining whether the patient has an increase in fluid requirements.

27. The method of claim 25, wherein determining whether the patient needs more fluids comprises estimating how much fluid is needed, based at least in part on how much fluid the patient has received between the first time and the second time in relation to the physical perturbation of the patient.

28. An apparatus, comprising:

a non-transitory computer readable medium having encoded thereon a set of instructions executable by one or more computers to:

receive a first set of physiological data from one or more sensors at a first time in relation to a physical perturbation of a patient, the one or more sensors monitoring physiological data of the patient, wherein the physiological data is cardiovascular data of the patient;

calculate a first set of compensatory reserve index ("CRI") values of the patient based on a comparison of the first set of physiological data to a model comprising a plurality of waveforms of reference data, each waveform of the plurality of waveforms corresponding to a respective CRI value determined from a ratio of intravascular volume loss at time t and intravascular volume loss at hemodynamic decompensation, wherein the first set of physiological data includes waveform data of the patient at the first time, wherein waveform data of the patient at the first time includes one or more first patient waveforms, wherein comparing the first set of physiological data against the model comprises comparing the waveform data of the patient against the plurality of waveforms of reference data, and determining a similarity between a respective first patient waveform of the one or more first patient waveforms and each of one or more waveforms of the plurality of waveforms of reference data individually, and wherein calculating a respective first CRI value of the first set of CRI values of the patient corresponding to the respective first patient waveform is based at least in part on respective similarities of the respective first patient waveform to each of the one or more waveforms of the plurality of waveforms of reference data individually;

receive a second set of physiological data from the one or more sensors at a second time in relation to the physical perturbation of the patient;

calculate a second set of CRI values of the patient based on a comparison of the second set of physiological data to the model, wherein the second set of physiological data includes waveform data of the patient at the second time;

based at least in part on a change between the first and second sets of CRI values, estimate a physiological state of the patient, wherein the change between the first and second sets of CRI values is compared against a CRI model separate from the model comprising the plurality of waveforms of reference data, wherein the CRI model relates changes in CRI value to the physiological state of the patient; and display on a display device, an estimate of the physiological state of the patient.

29. A system, comprising:

a processor; and a non-transitory computer readable medium having encoded thereon a set of instructions that, when executed by the processor, causes the system to:

receive a first set of physiological data from one or more sensors at a first time in relation to a physical perturbation of a patient, the one or more sensors monitoring physiological data of the patient, wherein the physiological data is cardiovascular data of the patient;

calculate a first set of compensatory reserve index ("CRI") values of the patient based on a comparison of the first set of physiological data to a model comprising a plurality of waveforms of reference data, each waveform of the plurality of waveforms corresponding to a respective CRI value determined from a ratio of intravascular volume loss at time t and intravascular volume loss at hemodynamic decompensation, wherein the first set of physiological data includes waveform data of the patient at the first time, wherein waveform data of the patient at the first time includes one or more first patient waveforms, wherein comparing the first set of physiological data against the model comprises comparing the waveform data of the patient against the plurality of waveforms of reference data, and determining a similarity between a respective first patient waveform of the one or more first patient waveforms and each of one or more waveforms of the plurality of waveforms of reference data individually, and wherein calculating a respective first CRI value of the first set of CRI values of the patient corresponding to the respective first patient waveform is based at least in part on respective similarities of the respective first patient waveform to each of the one or more waveforms of the plurality of waveforms of reference data individually;

receive a second set of physiological data from the one or more sensors at a second time in relation to the physical perturbation of the patient;

calculate a second set of CRI values of the patient based on a comparison of the second set of physiological data to the model, wherein the second set of physiological data includes waveform data of the patient at the second time;

based at least in part on a change between the first and second sets of CRI values, estimate a physiological state of the patient, wherein the change between the first and second sets of CRI values is compared against a CRI model separate from the model comprising the plurality of waveforms of reference data, wherein the CRI model relates changes in CRI value to the physiological state of the patient; and display on a display device, an estimate of the physiological state of the patient.

* * * * *